United States Patent
Helm et al.

(10) Patent No.: US 11,364,006 B2
(45) Date of Patent: Jun. 21, 2022

(54) SYSTEM AND METHOD FOR IMAGING A SUBJECT

(71) Applicant: Medtronic Navigation, Inc., Louisville, CO (US)

(72) Inventors: Patrick A. Helm, Milton, MA (US); Rasika A. Parkar, Waltham, MA (US); Robert J. Reddy, Broomfield, CO (US); Kyo C. Jin, Durham, NH (US); Seunghoon Nam, Bedford, MA (US); Andre Souza, Boylston, MA (US); Xiaodong Tao, Westwood, MA (US); David A. Garlow, Lynnfield, MA (US); John R. Martin, Franklin, MA (US)

(73) Assignee: Medtronic Navigation, Inc., Louisville, CO (US)

( * ) Notice: Subject to any disclaimer, the term of this patent is extended or adjusted under 35 U.S.C. 154(b) by 0 days.

(21) Appl. No.: 17/140,930

(22) Filed: Jan. 4, 2021

(65) Prior Publication Data
US 2021/0145392 A1 May 20, 2021

Related U.S. Application Data

(63) Continuation of application No. 16/233,753, filed on Dec. 27, 2018, now Pat. No. 10,881,371.

(51) Int. Cl.
*G01N 23/04* (2018.01)
*A61B 6/00* (2006.01)
(Continued)

(52) U.S. Cl.
CPC .......... *A61B 6/5241* (2013.01); *A61B 6/4035* (2013.01); *A61B 6/4452* (2013.01);
(Continued)

(58) Field of Classification Search
CPC ... A61B 6/5241; A61B 6/4035; A61B 6/4452; A61B 6/463; A61B 2090/3983; A61B 5/055; G01N 2223/401; G01N 23/04
See application file for complete search history.

(56) References Cited

U.S. PATENT DOCUMENTS

| 3,509,341 A | 4/1970 | Hindel et al. |
| 4,020,356 A | 4/1977 | Brahme |

(Continued)

FOREIGN PATENT DOCUMENTS

| DE | 102012207626 A1 | 11/2013 |
| EP | 861556 B1 | 9/2007 |

(Continued)

OTHER PUBLICATIONS

Fang, et al., Multi-Perspective Panoramas Of Long Scenes, 2012 IEEE International Conference On Multimedia And Expo.
(Continued)

*Primary Examiner* — David P Porta
*Assistant Examiner* — Fani Polyzos Boosalis
(74) *Attorney, Agent, or Firm* — Harness, Dickey & Pierce, P.L.C.

(57) ABSTRACT

A method and system is disclosed for acquiring image data of a subject. The image data can be collected with an imaging system in a selected manner and/or motion. More than one projection may be combined to generate and create a selected view of the subject.

21 Claims, 11 Drawing Sheets

(51) Int. Cl.
*G06T 3/00* (2006.01)
*A61B 90/00* (2016.01)
*A61B 5/055* (2006.01)

(52) U.S. Cl.
CPC .............. *A61B 6/463* (2013.01); *G01N 23/04* (2013.01); *G06T 3/0068* (2013.01); *A61B 5/055* (2013.01); *A61B 2090/3983* (2016.02); *G01N 2223/401* (2013.01)

(56) References Cited

U.S. PATENT DOCUMENTS

| | | | |
|---|---|---|---|
| 4,613,983 | A | 9/1986 | Yedid et al. |
| 4,731,807 | A | 3/1988 | Plessis et al. |
| 4,809,312 | A | 2/1989 | Annis |
| 4,896,037 | A | 1/1990 | Shimura et al. |
| 5,214,686 | A | 5/1993 | Webber |
| 5,224,136 | A | 6/1993 | Toth et al. |
| 5,396,534 | A | 3/1995 | Thomas |
| 5,648,997 | A | 7/1997 | Chao |
| 5,677,943 | A | 10/1997 | Hoebel |
| 5,745,544 | A | 4/1998 | Mazess |
| 5,747,812 | A | 5/1998 | DiFilippo |
| 5,771,269 | A | 6/1998 | Chao |
| 5,838,765 | A | 11/1998 | Gershman et al. |
| 6,081,582 | A | 6/2000 | Mazess et al. |
| 6,097,833 | A | 8/2000 | Lobregt et al. |
| 6,134,297 | A | 10/2000 | Chao |
| 6,185,271 | B1 | 2/2001 | Kinsinger |
| 6,301,334 | B1 | 10/2001 | Tybinkowski et al. |
| 6,396,902 | B2 | 5/2002 | Tybinkowski et al. |
| 6,556,657 | B1 | 4/2003 | Tybinkowski et al. |
| 6,587,598 | B1 | 7/2003 | Devillers et al. |
| 6,666,579 | B2 | 12/2003 | Jensen |
| 6,793,390 | B2 | 9/2004 | Wang et al. |
| 6,895,106 | B2 | 5/2005 | Wang et al. |
| 6,940,948 | B1 | 9/2005 | Tretiakov et al. |
| 6,944,265 | B2 | 9/2005 | Warp et al. |
| 6,969,861 | B2 | 11/2005 | Shoji et al. |
| 7,073,939 | B2 | 7/2006 | Spahn |
| 7,142,632 | B2 | 11/2006 | Atzinger et al. |
| 7,177,455 | B2 | 2/2007 | Warp et al. |
| 7,391,846 | B2 | 6/2008 | Verdonck et al. |
| 7,505,554 | B2 | 3/2009 | Ting |
| 7,555,100 | B2 | 6/2009 | Wang et al. |
| 8,014,575 | B2 | 9/2011 | Weiss et al. |
| 8,126,119 | B2 | 2/2012 | Kurochi |
| 8,213,572 | B2 * | 7/2012 | Minnigh .............. A61B 6/588 378/62 |
| 8,238,631 | B2 | 8/2012 | Hartmann et al. |
| 8,457,377 | B2 | 6/2013 | Weiss |
| 8,693,622 | B2 | 4/2014 | Graumann et al. |
| 8,873,709 | B2 | 10/2014 | Kimura |
| 8,899,832 | B2 | 12/2014 | Fabrizio |
| 9,060,733 | B2 | 6/2015 | Bruder et al. |
| 9,109,998 | B2 | 8/2015 | Nathaniel et al. |
| 9,121,809 | B2 | 9/2015 | Cox et al. |
| 9,125,572 | B2 | 9/2015 | Noo et al. |
| 9,689,811 | B2 | 6/2017 | Cox et al. |
| 9,980,682 | B2 | 5/2018 | Ahn et al. |
| 10,082,473 | B2 | 9/2018 | Pack et al. |
| 2001/0001011 | A1 | 5/2001 | Saib |
| 2006/0203959 | A1 | 9/2006 | Spartiotis et al. |
| 2007/0078336 | A1 | 4/2007 | Toth |
| 2008/0165923 | A1 | 7/2008 | Muller |
| 2010/0290690 | A1 | 11/2010 | Hartmann et al. |
| 2011/0075810 | A1 | 3/2011 | Sendai |
| 2011/0261926 | A1 | 10/2011 | Hangartner et al. |
| 2012/0099772 | A1 | 4/2012 | Helm et al. |
| 2012/0106705 | A1 | 5/2012 | Mikami et al. |
| 2012/0250822 | A1 | 10/2012 | Helm et al. |
| 2013/0202087 | A1 | 8/2013 | Cox |
| 2013/0287164 | A1 | 10/2013 | Rogers |
| 2014/0146948 | A1 | 5/2014 | Zhang et al. |
| 2014/0211913 | A1 | 7/2014 | Pan et al. |
| 2015/0150523 | A1 | 6/2015 | Sirpad et al. |
| 2015/0250441 | A1 | 9/2015 | Okuno et al. |
| 2015/0282774 | A1 | 10/2015 | Lee et al. |
| 2016/0071291 | A1 | 3/2016 | Samsonov et al. |
| 2016/0220207 | A1 * | 8/2016 | Jouhikainen ......... A61B 6/4021 |
| 2016/0343462 | A1 | 11/2016 | Karch et al. |
| 2017/0325776 | A1 | 11/2017 | Cox et al. |
| 2018/0049711 | A1 | 2/2018 | Ji et al. |
| 2018/0168522 | A1 | 6/2018 | Budde et al. |
| 2018/0310899 | A1 | 11/2018 | Garlow et al. |

FOREIGN PATENT DOCUMENTS

| | | |
|---|---|---|
| EP | 2592728 A2 | 5/2013 |
| JP | 2007267787 A | 10/2007 |
| JP | 2008000220 A | 1/2008 |

OTHER PUBLICATIONS

Geiger, et al., Digital Radiography Of Scoliosis With A Scanning Method: Initial Evaluation, Radiology 2001; 218:402-410.

Kumar et al., Automatic Image Alignment and Stitching of Medical Images With Seam Blending, International Journal Of Medical, Health, Biomedical, Bioengineering And Pharmaceutical Engineering vol. 4, No. 5, 2010.

Szeliki, Image Alignment And Stitching: A Tutorial, Technical Report, Dec. 10, 2006.

Van Eeuwijk, et al., A Novel Method For Digital X-Ray Imaging Of The Complete Spine, Basic Tools And Applications in Spine Surgery, 1997.

Verdonck, et al., Image Quality And X-Ray Dose For Translation Reconstruction Overview Imaging Of The Spine, Colon And Legs, International Congress Series 1230 (2001) 531-537.

Wang, et al., Parallax-Free Intra-Operative X-Ray Image Stitching, Medical Image Analysis 14 (2010) 674-686.

Yaniv, et al., Long Bone Panoramas From Fluoroscopic X-Ray Images, IEEE Transactions On Medical Imaging, vol. 23, No. 1, Jan. 2004.

International Search Report and Written Opinion dated Mar. 27, 2020 in corresponding/related International Application No. PCT/US2019/068430.

International Search Report and Written Opinion dated Apr. 2, 2020 in corresponding/related International Application No. PCT/US2019/068437.

International Search Report and Written Opinion dated Apr. 2, 2020 in corresponding/related International Application No. PCT/US2019/068432.

U.S. Appl. No. 16/233,753, U.S. Pat. No. 10,881,371, filed Dec. 27, 2018, Helm, et al.

* cited by examiner

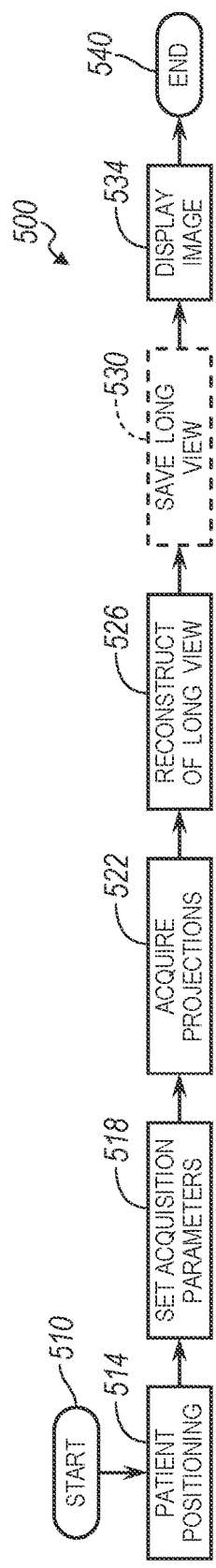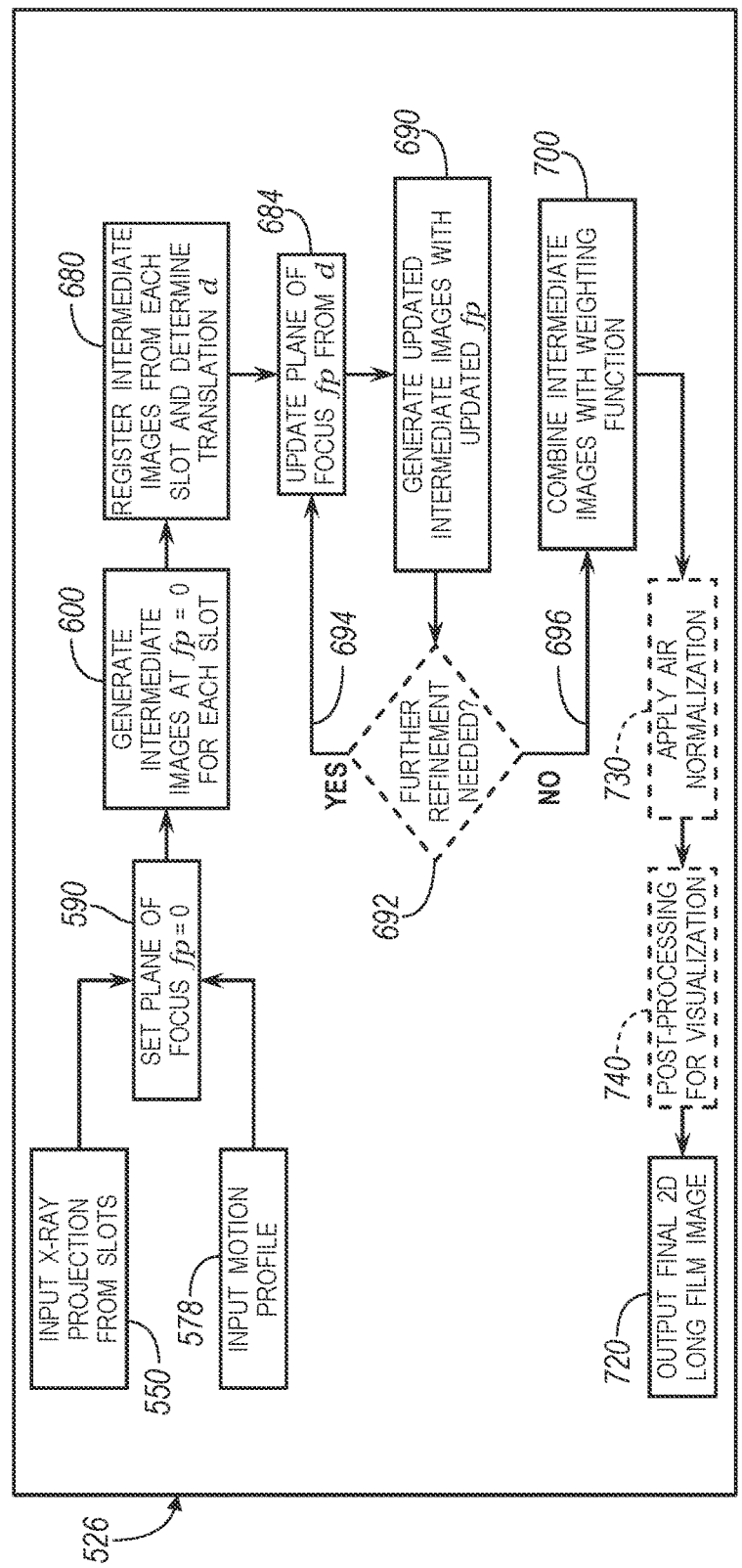

US 11,364,006 B2

SYSTEM AND METHOD FOR IMAGING A SUBJECT

CROSS-REFERENCE TO RELATED APPLICATIONS

This application is a continuation of U.S. patent application Ser. No. 16/233,753 filed on Dec. 27, 2018. This application also includes subject matter similar to that disclosed in concurrently filed U.S. patent application Ser. Nos. 16/233,809 and 16/233,855 both filed on Dec. 27, 2018. The entire disclosures of each of the above applications are incorporated herein by reference.

FIELD

The present disclosure relates to imaging a subject, and particularly to a system to acquire image data for generating a selected view of the subject.

BACKGROUND

This section provides background information related to the present disclosure which is not necessarily prior art.

A subject, such as a human patient, may undergo a procedure. The procedure may include a surgical procedure to correct or augment an anatomy of the subject. The augmentation of the anatomy can include various procedures, such as movement or augmentation of bone, insertion of an implant (i.e. an implantable device), or other appropriate procedures.

A surgeon can perform the procedure on the subject with images of the subject that are based on projections of the subject. The images may be generated with imaging systems such as a magnetic resonance imaging (MRI) system, computed tomography (CT) system, fluoroscopy (e.g. C-Arm imaging systems), or other appropriate imaging systems.

SUMMARY

This section provides a general summary of the disclosure, and is not a comprehensive disclosure of its full scope or all of its features.

According to various embodiments, a system to acquire image data of a subject with an imaging system may use x-rays. The subject may be a living patient (e.g. a human patient). The subject may also be a non-living subject, such as an enclosure, a casing, etc. The imaging system may include a moveable source and/or detector that is moveable relative to the subject.

An imaging system may include a movable source and/or detector to create a plurality of projections of a subject. The plurality of projections may be acquired in a linear path of movement of the source and/or detector. The plurality of projections may then be combined, such as by stitching together, to generate or form a long view (also referred to as a long film). The long view may be a two-dimensional view of the subject.

In various embodiments, the imaging system may acquire a plurality of projections at different perspectives relative to the subject. The different perspectives may be generated due to a parallax effect between different paths of x-rays from a single source to the detector through the subject. The parallax effect may allow for different views of the same position of the subject. The parallax effect may be formed due to a filter having a plurality of slits or slots through which the x-rays pass and impinge upon the detector. Accordingly, movement of the source and/or detector relative to the subject may allow for acquisition of a plurality of projections through the subject including a parallax effect. The plurality of projections may then be stitched to form a plurality of long views of the subject due to movement of the source and/or detector.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 6 is a flow chart performing a long view or long film image, according to various embodiments;

FIG. 7 is a detailed flow chart of a portion of the long view method;

Corresponding reference numerals indicate corresponding parts throughout the several views of the drawings.

DETAILED DESCRIPTION

Example embodiments will now be described more fully with reference to the accompanying drawings.

Figure 1:
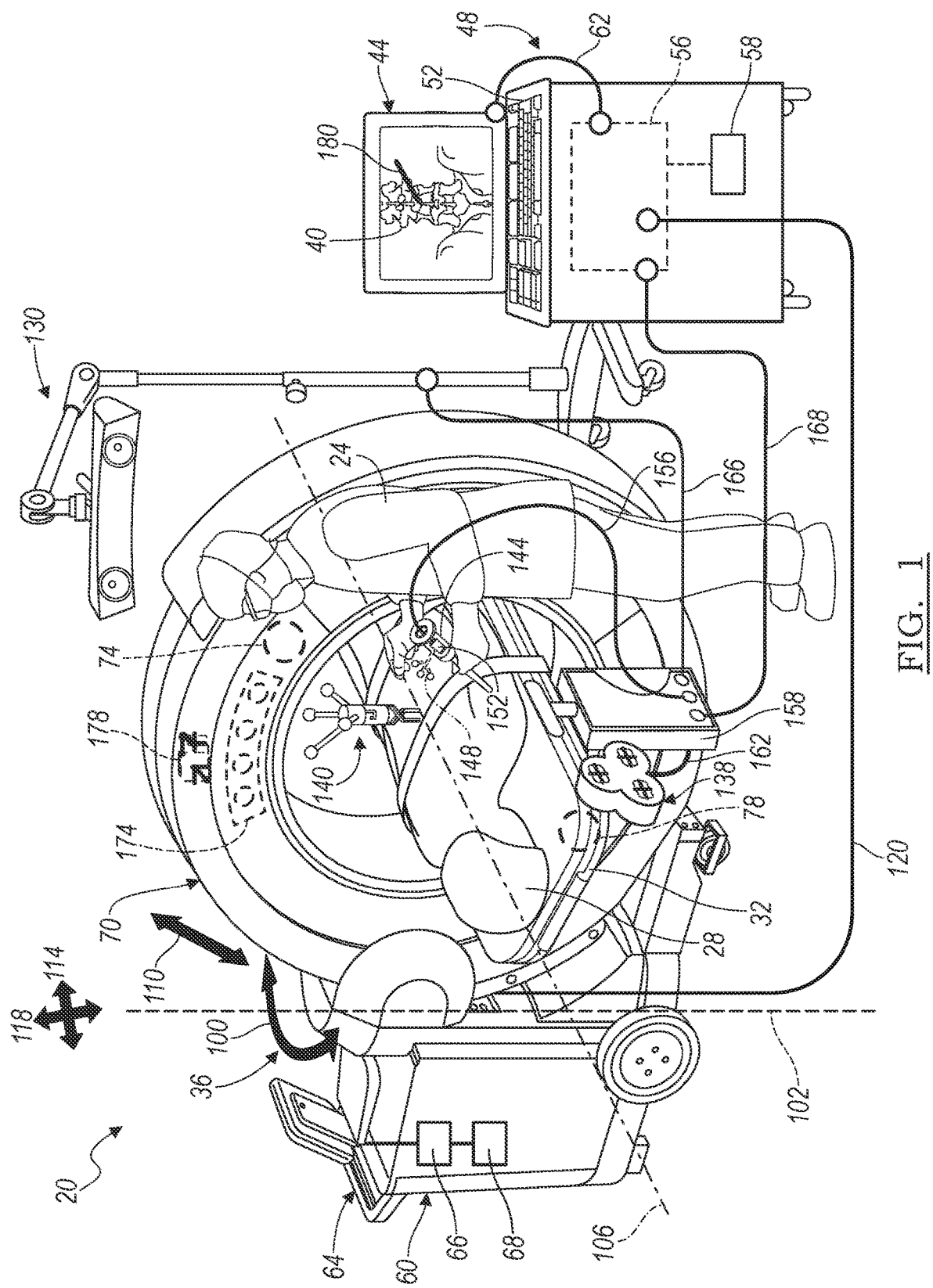
FIG. 1 is an environmental view of an imaging system in an operating theatre.

With reference to FIG. 1, a schematic view of a procedure room 20 is illustrated. A user 24, such as a surgeon, can perform a procedure on a subject, such as a patient 28. The subject may be placed on a support, such as a table 32 for a selected portion of the procedure. The table 32 may not interfere with image data acquisition with an imaging system 36. In performing the procedure, the user 12 can use the imaging system 36 to acquire image data of the patient 28 to allow a selected system to generate or create images to assist in performing a procedure. Images generated with the image data, such as a model (such as a three-dimensional (3D) image), long views, single projections views, etc. can be generated using the image data and displayed as an image 40 on a display device 44. The display device 44 can be part of and/or connected to a processor system 48 that includes an input device 52, such as a keyboard, and a processor 56, which can include one or more processors or microprocessors incorporated with the processing system 48 along with selected types of non-transitory and/or transitory memory 58. A connection 62 can be provided between the processor 56 and the display device 44 for data communication to allow driving the display device 44 to display or illustrate the image 40. The processor 56 may be any appropriate type of processor such as a general purpose processor that executes instructions included in a program or an application specific processor such as an application specific integrated circuit.

The imaging system 36 can include an O-Arm® imaging system sold by Medtronic Navigation, Inc. having a place of business in Louisville, Colo., USA. The imaging system 36, including the O-Arm® imaging system, or other appropriate imaging systems may be in use during a selected procedure, such as the imaging system described in U.S. Patent App. Pubs. 2012/0250822, 2012/0099772, and 2010/0290690, all incorporated herein by reference.

The imaging system 36, when, for example, including the O-Arm® imaging system, may include a mobile cart 60 that includes a controller and/or control system 64. The control system 64 may include a processor and/or processor system 66 (similar to the processor 56) and a memory 68 (e.g. a non-transitory memory). The memory 68 may include various instructions that are executed by the processor 66 to control the imaging system 36, including various portions of the imaging system 36.

The imaging system 36 may include further addition portions, such as an imaging gantry 70 in which is positioned a source unit (also referred to as an assembly) 74 and a detector unit (also referred to as an assembly) 78. The gantry 70 is moveably connected to the mobile cart 60. The gantry 70 may be O-shaped or toroid shaped, wherein the gantry 70 is substantially annular and includes walls that form a volume in which the source unit 74 and detector 78 may move. The mobile cart 60 may also be moved, and can be moved from one operating theater to another and or another room. The gantry 70 can move relative to the cart 60, as discussed further herein. This allows the imaging system 36 to be mobile and moveable relative to the subject 28 thus allowing it to be used in multiple locations and with multiple procedures without requiring a capital expenditure or space dedicated to a fixed imaging system.

The processor 66 may be a general purpose processor or a specific application processor. The memory system 68 may be a non-transitory memory such as a spinning disk or solid state non-volatile memory. In various embodiments, the memory system may include instructions to be executed by the processor 66 to perform functions and determine results, as discussed herein.

In various embodiments, the imaging system 36 may include an imaging system that acquires images and/or image data by the use of emitting x-rays and detecting interactions and/or attenuations of the x-rays with the subject 28. Thus, x-ray imaging may be an imaging modality. It is understood that other imaging modalities are possible.

Figure 2:
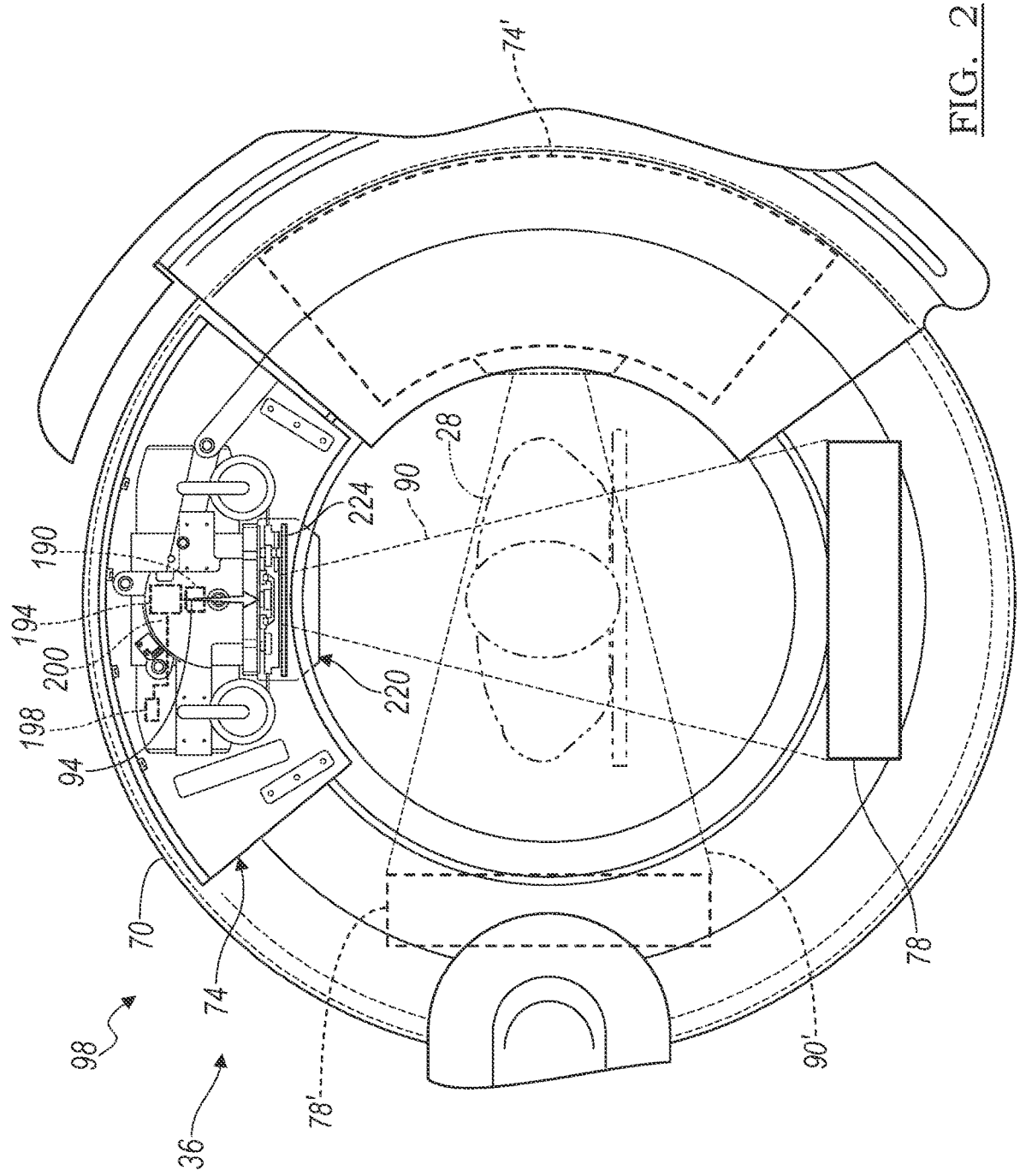
FIG. 2 is a detailed schematic view of an imaging system with a dual energy source system.

Thus, the imaging system 36 that includes the source unit 74 may be an x-ray emitter that can emit x-rays through the patient 28 to be detected by the detector 78. As is understood by one skilled in the art, the x-rays emitted by the source 74 can be emitted in a cone 90 along a selected main vector 94 and detected by the detector 78, as illustrated in FIG. 2. The source 74 and the detector 78 may also be referred to together as a source/detector unit 98, especially wherein the source 74 is generally diametrically opposed (e.g. 180 degrees apart) from the detector 78 within the gantry 70.

The imaging system 36 may move, as a whole or in part, relative to the subject 28. For example, the source 74 and the detector 78 can move in a 360° motion around the patient 28. The movement of the source/detector unit 98 within the gantry 70 may allow the source 74 to remain generally 180° opposed (such as with a fixed inner gantry or rotor or moving system) to the detector 78. Thus, the detector 78 may be referred to as moving around (e.g. in a circle or spiral) the subject 28 and it is understood that the source 74 is remaining opposed thereto, unless disclosed otherwise.

Also, the gantry 70 can move isometrically (also referred as "wag" relative to the subject 28 generally in the direction of arrow 100 around an axis 102, such as through the cart 60, as illustrated in FIG. 1. The gantry 34 can also tilt relative to a long axis 106 of the patient 28 illustrated by arrows 110. In tilting, a plane of the gantry 70 may tilt or form a non-orthogonal angle with the axis 106 of the subject 28.

The gantry 70 may also move longitudinally in the direction of arrows 114 along the line 106 relative to the subject 28 and/or the cart 60. Also, the cart 60 may move to move the gantry 70. Further, the gantry 70 can move up and down generally in the direction of arrows 118 relative to the cart 30 and/or the subject 28, generally transverse to the axis 106 and parallel with the axis 102.

The movement of the imaging system 60, in whole or in part is to allow for positioning of the source/detector unit (SDU) 98 relative to the subject 28. The imaging device 36 can be precisely controlled to move the SDU 98 relative to the subject 28 to generate precise image data of the subject 28. The imaging device 36 can be connected with the processor 56 via a connection 120, which can include a wired or wireless connection or physical media transfer from the imaging system 36 to the processor 56. Thus, image data collected with the imaging system 36 can be transferred to the processing system 56 for navigation, display, reconstruction, etc.

The source 74, as discussed herein, may include one or more sources of x-rays for imaging the subject 28. In various embodiments, the source 74 may include a single source that may be powered by more than one power source to generate and/or emit x-rays at different energy characteristics. Further, more than one x-ray source may be the source 74 that may be powered to emit x-rays with differing energy characteristics at selected times.

According to various embodiments, the imaging system 36 can be used with an un-navigated or navigated procedure. In a navigated procedure, a localizer and/or digitizer, including either or both of an optical localizer 130 and/or an electromagnetic localizer 138 can be used to generate a field and/or receive and/or send a signal within a navigation domain relative to the subject 28. The navigated space or navigational domain relative to the subject 28 can be registered to the image 40. Correlation, as understood in the art, is to allow registration of a navigation space defined within the navigational domain and an image space defined by the image 40. A patient tracker or dynamic reference frame 140 can be connected to the subject 28 to allow for a dynamic registration and maintenance of registration of the subject 28 to the image 40.

The patient tracking device or dynamic registration device 140 and an instrument 144 can then be tracked relative to the subject 28 to allow for a navigated procedure. The instrument 144 can include a tracking device, such as an optical tracking device 148 and/or an electromagnetic tracking device 152 to allow for tracking of the instrument 144 with either or both of the optical localizer 130 or the electromagnetic localizer 138. A navigation/probe interface device 158 may have communications (e.g. wired or wireless) with the instrument 144 (e.g. via a communication line 156), with the electromagnetic localizer 138 (e.g. via a communication line 162), and/or the optical localizer 60 (e.g. via a communication line 166). The interface 158 can also communicate with the processor 56 with a communication line 168 and may communicate information (e.g. signals) regarding the various items connected to the interface 158. It will be understood that any of the communication lines can be wired, wireless, physical media transmission or movement, or any other appropriate communication. Nevertheless, the appropriate communication systems can be provided with the respective localizers to allow for tracking of the instrument 144 relative to the subject 28 to allow for illustration of a tracked location of the instrument 144 relative to the image 40 for performing a procedure.

One skilled in the art will understand that the instrument 144 may be any appropriate instrument, such as a ventricular or vascular stent, spinal implant, neurological stent or stimulator, ablation device, or the like. The instrument 144 can be an interventional instrument or can include or be an implantable device. Tracking the instrument 144 allows for viewing a location (including x,y,z position and orientation) of the instrument 144 relative to the subject 28 with use of the registered image 40 without direct viewing of the instrument 144 within the subject 28.

Further, the imaging system 36, such as the gantry 70, can include an optical tracking device 174 and/or an electromagnetic tracking device 178 to be tracked with the respective optical localizer 130 and/or electromagnetic localizer 138. Accordingly, the imaging device 36 can be tracked relative to the subject 28 as can the instrument 144 to allow for initial registration, automatic registration, or continued registration of the subject 28 relative to the image 40. Registration and navigated procedures are discussed in the above incorporated U.S. Pat. No. 8,238,631, incorporated herein by reference. Upon registration and tracking of the instrument 144, an icon 180 may be displayed relative to, including overlaid on, the image 40.

With continuing reference to FIG. 2, according to various embodiments, the source 74 can include a single x-ray tube assembly 190 that can be connected to a switch 194 that can interconnect a first power source 198 via a connection or power line 200. As discussed above, X-rays can be emitted from the x-ray tube 190 generally in the cone shape 90 towards the detector 78 and generally in the direction from the x-ray tube 190 as indicated by arrow, beam arrow, beam or vector 94. The switch 194 can switch power on or off to the tube 190 to emit x-rays of selected characteristics, as is understood by one skilled in the art. The vector 94 may be a central vector or ray within the cone 90 of x-rays. An x-ray beam may be emitted as the cone 90 or other appropriate geometry. The vector 94 may include a selected line or axis relevant for further interaction with the beam, such as with a filter member, as discussed further herein.

The subject 28 can be positioned within the x-ray cone 94 to allow for acquiring image data of the subject 28 based upon the emission of x-rays in the direction of vector 94 towards the detector 78.

The x-ray tube 190 may be used to generate two dimension (2D) x-ray projections of the subject 28, including selected portions of the subject 28, or any area, region or volume of interest, in light of the x-rays impinging upon or being detected on a 2D or flat panel detector, as the detector 78. The 2D x-ray projections can be reconstructed, as discussed herein, to generate and/or display three-dimensional (3D) volumetric models of the subject 28, selected portion of the subject 28, or any area, region or volume of interest. As discussed herein, the 2D x-ray projections can be image data acquired with the imaging system 36, while the 3D volumetric models can be generated or model image data.

For reconstructing or forming the 3D volumetric image, appropriate algebraic techniques include Expectation maximization (EM), Ordered Subsets EM (OS-EM), Simultaneous Algebraic Reconstruction Technique (SART) and Total Variation Minimization (TVM), as generally understood by those skilled in the art. The application to perform a 3D volumetric reconstruction based on the 2D projections allows for efficient and complete volumetric reconstruction. Generally, an algebraic technique can include an iterative process to perform a reconstruction of the subject 28 for display as the image 40. For example, a pure or theoretical image data projection, such as those based on or generated from an atlas or stylized model of a "theoretical" patient, can be iteratively changed until the theoretical projection images match the acquired 2D projection image data of the subject 28. Then, the stylized model can be appropriately altered as the 3D volumetric reconstruction model of the acquired 2D projection image data of the selected subject 28 and can be used in a surgical intervention, such as navigation, diagnosis, or planning. The theoretical model can be associated with theoretical image data to construct the theoretical model. In this way, the model or the image data 40 can be built based upon image data acquired of the subject 28 with the imaging device 36.

With continuing reference to FIG. 2, the source 74 may include various elements or features that may be moved relative to the x-ray tube 190. In various embodiments, for example, a collimator 220 may be positioned relative to the x-ray tube 190 to assist in forming the cone 90 relative to the subject 28. The collimator 220 may include various features such as movable members that may assist in positioning one or more filters within the cone 90 of the x-rays prior to reaching the subject 28. Further, as discussed further herein, various filters may be used to shape the x-ray beam, such as shaping the cone 90, into a selected shape prior to reaching the subject 28. In various embodiments, as discussed herein, the x-rays may be formed into a thin fan or plane to reach and pass through the subject 28 and be detected by the detector 78.

Accordingly, the source 74 including the collimator 220 may include a filter assembly 224. The filter assembly 224 may include one or more portions that allow for moving a filter relative to the x-ray tube 190 to shape and/or position the x-rays prior to reaching the subject 28. For example, with reference to FIG. 3, the filter assembly 224 may include a stage 228. The stage 228 may be positioned relative to the x-ray tube 190 and may substantially block all x-rays and/or define an initiation of the cone 90 as the x-rays pass through a stage exposure opening 232. The stage opening 232 may be an opening or passage through the stage 228 that allows x-rays to exit the x-ray tube 190 and form the cone 90.

Figure 3:
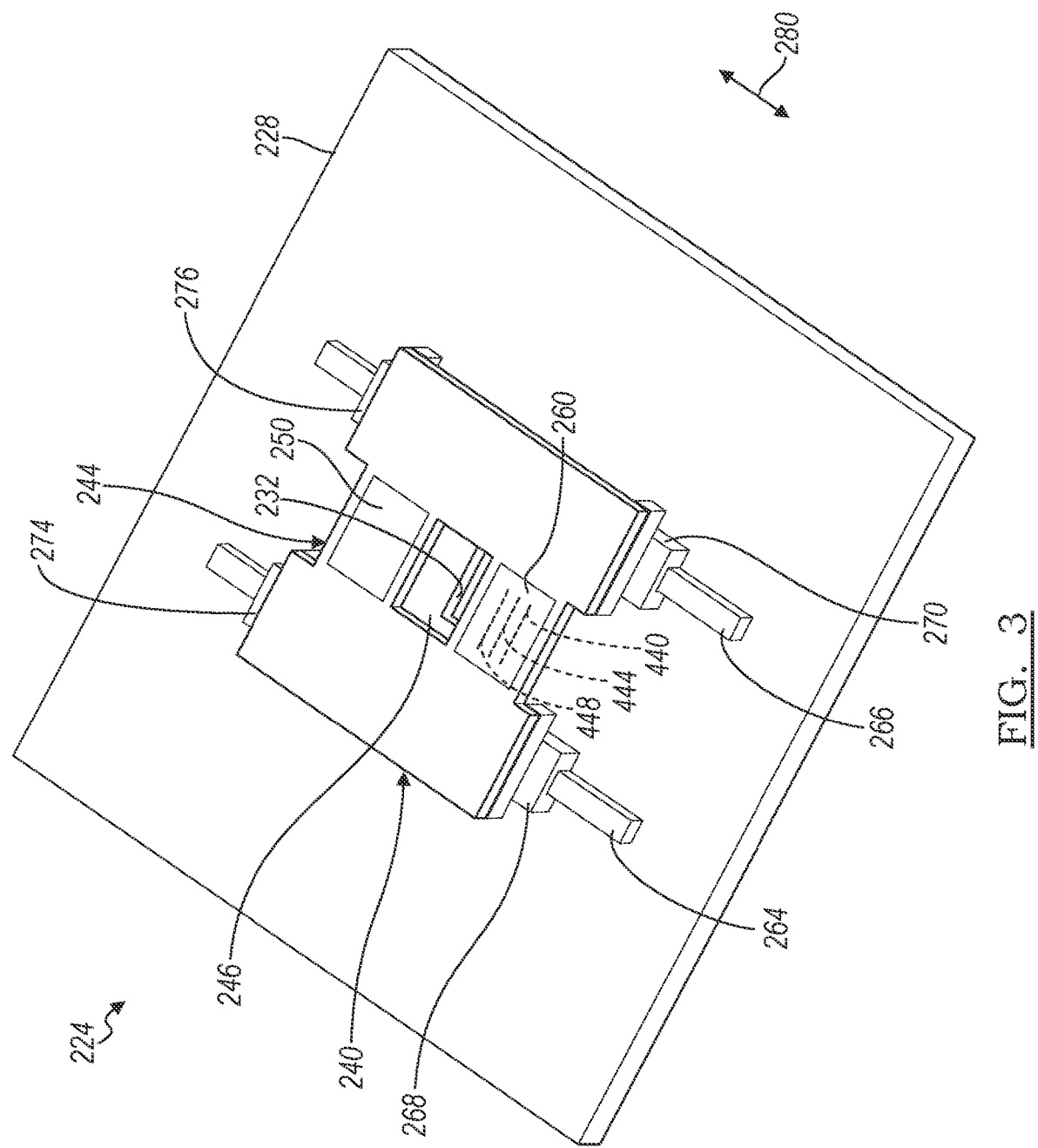
FIG. 3 is a perspective view of a filter assembly, according to various embodiments.

As illustrated in FIG. 3, a filter holding assembly 240 may include a movable filter holder or ladder 244. The filter ladder 244 may include one or more filter holding positions such as a first open position 246, a first filter or solid filter member 250, and a third or slot filter member 260, as discussed further herein. The filter ladder 244 may move on one or more rails, such as a first rail 264 and a second rail 266. The filter ladder 244 may be connected with one or more carrier members, such as a ladder car including a first carrier 268 that moves along the first rail 264 and a second carrier member 270 that moves along the second rail 266. It is understood that opposite or opposing carrier members may also be provided to ensure smoothness and/or selected planar movement of the filter ladder 244, therefore including a third carrier 274 and a fourth carrier 276. The third and fourth carriers 274, 276 may ride on the respective rails 264, 266 as the first and second carriers 268, 270. Accordingly, the filter ladder 244 may generally move in the direction of the double headed arrow 280 to selectively position the open filter portion 246, the solid filter portion 250, or the slot filter portion 260 relative to the aperture or passage opening 232 to allow x-rays to form the beam 90 or otherwise impinge on the subject 28, as discussed further herein. The filter assembly 224 may be used to augment an emission of x-rays from the x-ray tube 190 to assist in generating an image or image data of the subject 28, as discussed further herein.

The filter carrier or filter ladder 244 may be moved by selected mechanisms, such as servos or drive motors that are associated with the respective carriers 268, 270, 274, 276, or other appropriate mechanisms. Moving the filter ladder 244 may be controlled by the user 24, such as through manual input, and/or instructions provided to the imaging system 26. For example, the control system 64 may execute selected instructions to move the filter carrier 244 in a selected manner. Further, the control system 64 may move the filter carrier 244 at a selected time based upon selected inputs, such as inputs from the user 24, regarding selected images or image data to be acquired of the subject 28. Accordingly, the filter assembly 224 may be controlled by the controller 64 and/or any other appropriate controller, such as the processor system 48.

Figure 4A:
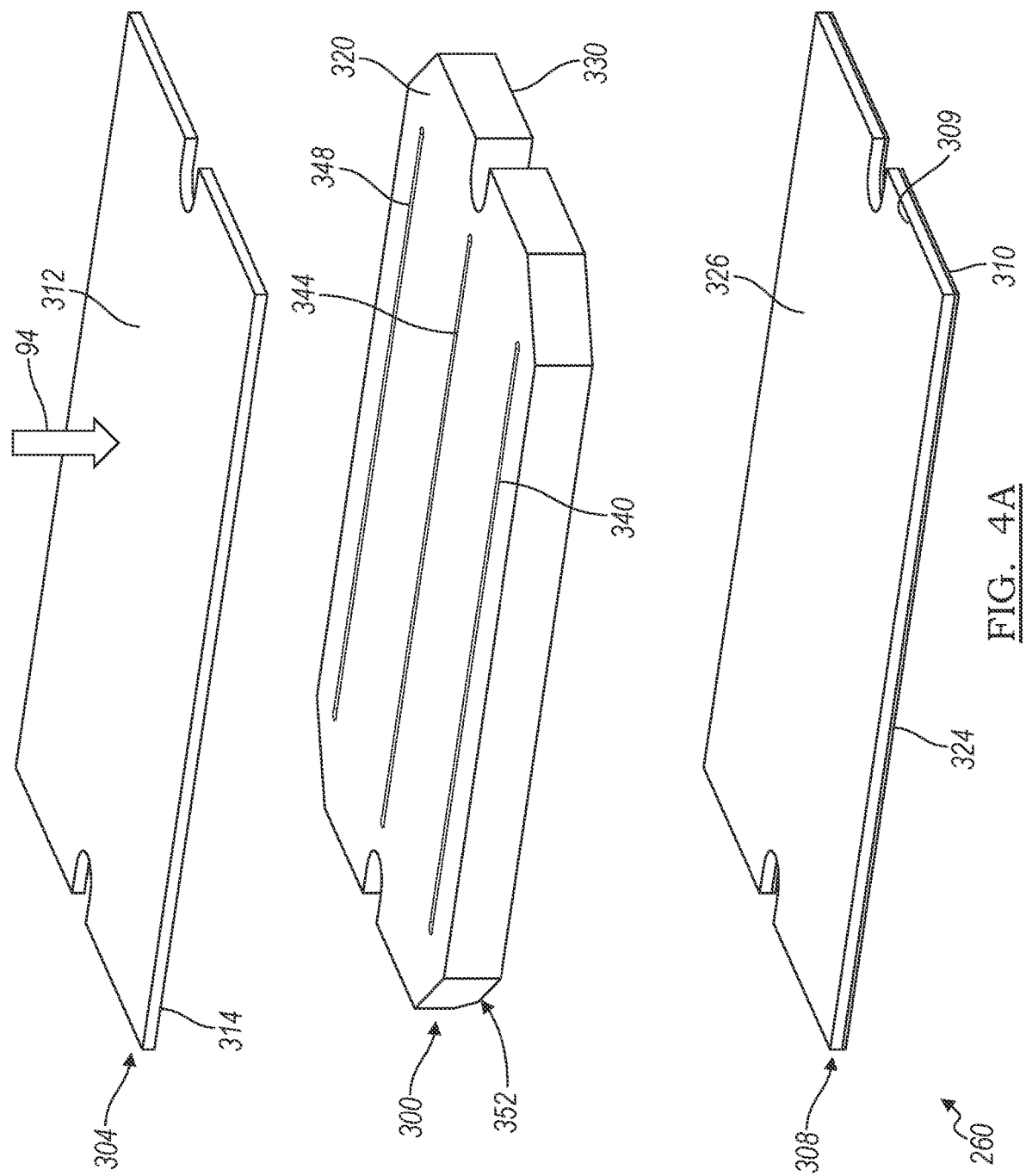
FIG. 4A is an exploded view of a slot filter assembly, according to various embodiments.
Figure 4B:
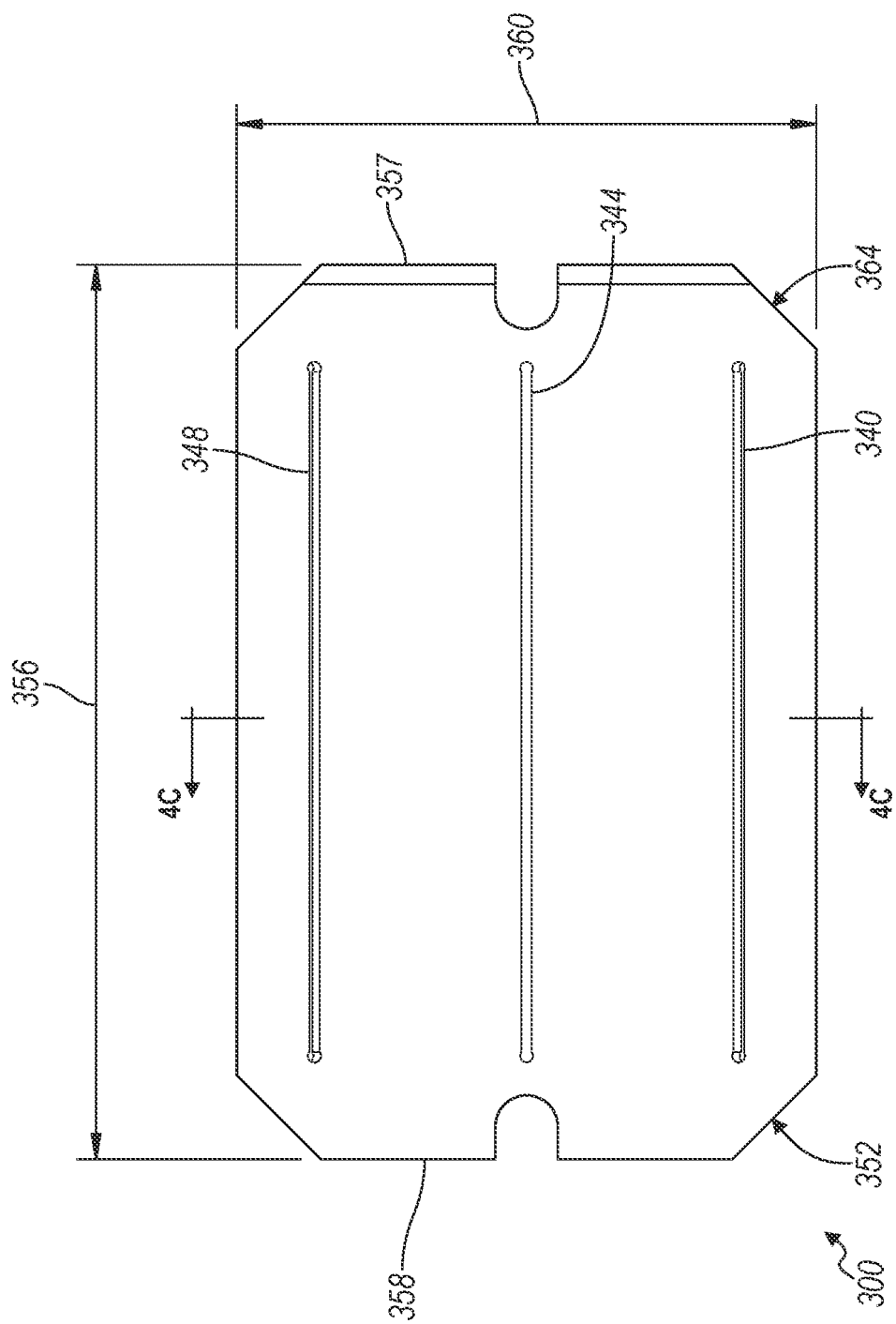
FIG. 4B is a top plan view of a slot filter body, according to various embodiments.
Figure 4C:
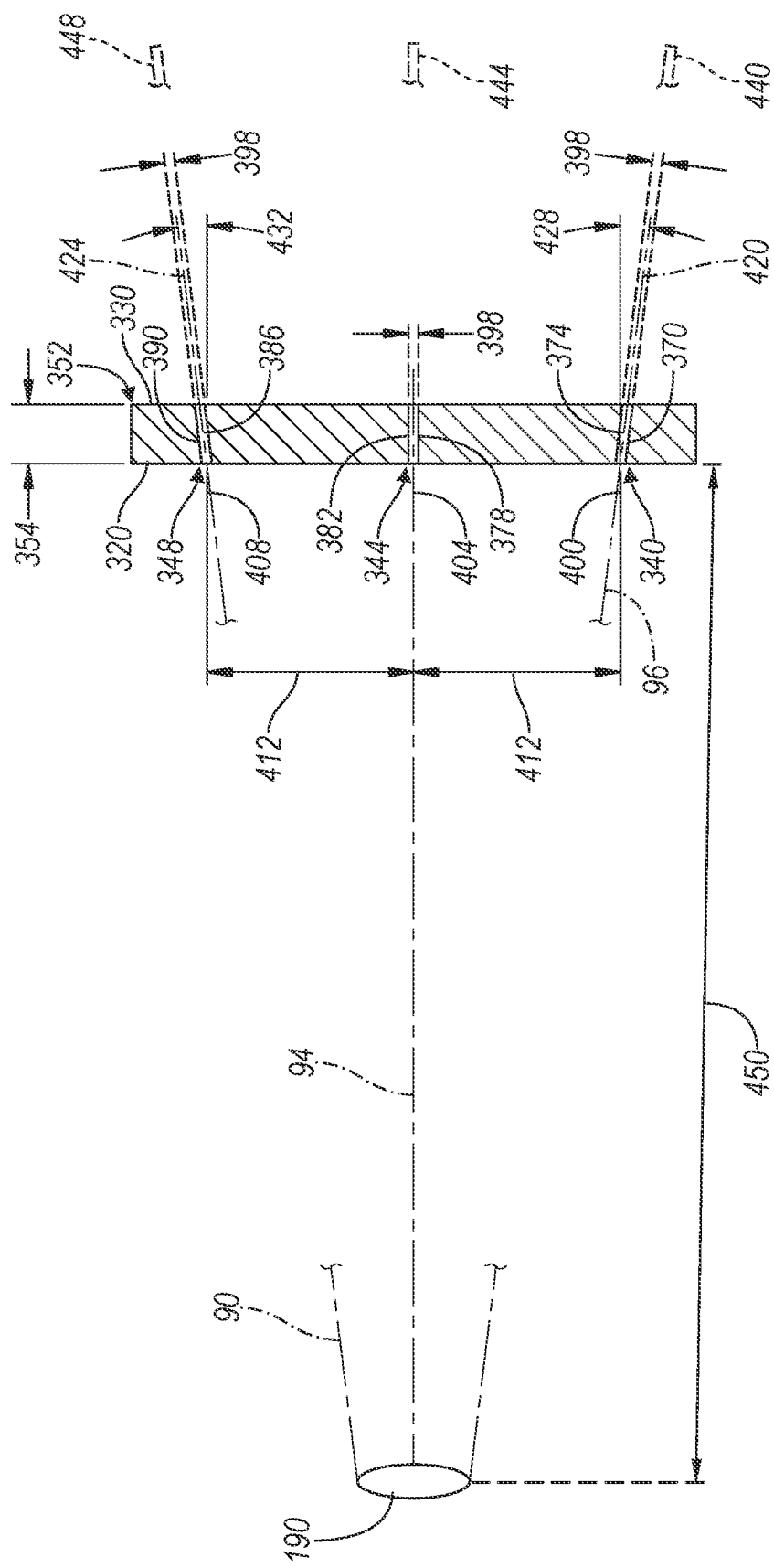
FIG. 4C is a cross-sectional view of a slot filter body that's about line 4C of FIG. 4B.

With reference to FIG. 4A, FIG. 4B, and FIG. 4C the slot filter assembly 260 is illustrated in greater detail. The slot filter assembly 260 may include a filter assembly that is formed of one or more members. It is understood, however, that the slot filter assembly may be formed of a single member including only the slot filter body 352, as discussed further herein. In various embodiments, the slot filter assembly 260 includes a slotted member or portion 300 that may be sandwiched between or placed between a first member or sheet 304 and a second member or sheet 308. It is understood, however, that the slotted member is not placed between the first member 304 and the second member 308. The first and second members 304, 308 may both be placed on a single side and/or incorporated into a single member placed on a single side of the slotted member 300. In various embodiments, however, the first and second members 304, 308 are solid and assist in ensure that slots 340, 344, 348 (discussed further herein) remain free and clear of debris.

The first sheet 304 may be formed of a selected material, such as substantially pure aluminum (i.e. pure aluminum as generally available to one skilled in the art), aluminum alloy, or other appropriate aluminum material. The top member 304 may include a first or exterior side 312 and a bottom or contact side 314. The two sides or surfaces 312, 314 may be substantially planar. The bottom or second side 314 may contact a first side 320 of the slotted member 300. The second side 314 may be adhered to the first side 320, such as with a selected adhesive or bonding member, such as an adhesive transfer tape. The thickness, or distance between the first side 312 and the second side 314 may be about 0.01 inches (in) to about 0.05 in, including about 0.02 in (about 0.5 millimeters (mm)).

The second layer or member 308 may include a first surface 324 that may be an exterior surface and a second surface or interior surface 326. The second surface 326 may contact a bottom or second surface 330 of the slotted member 300. The second layer 308, however, may include or be formed as a dual material construction formed of an aluminum portion 309 (formed of the same or similar aluminum materials as discussed above) and a copper portion 310 (e.g. substantially pure copper). In various embodiments, the first portion may be 0.5 mm thick 1100 series aluminum bonded to 0.1 mm 99% pure copper with a selected material, such as Scotch brand adhesive 924. The entire second layer, however, may have a thickness of about 0.01 inches (in) to about 0.05 in, including about 0.02 in (about 0.5 millimeters (mm)). The sheets 304, 308 will generally have a parameter that is generally coextensive with edges of the slotted member 300.

The slotted member 300 may include dimensions, as discussed further herein. The slotted member 300 may be formed of a selected material such as tungsten carbide having a selected amount of tungsten, such as about 90% minimum tungsten. In various embodiments, the tungsten carbide is ANSI grade C2 tungsten carbide. For example, the tungsten carbide may be TECHMET grade TMK-22 tungsten carbide having a about 94% tungsten carbide and 6% cobalt. In various embodiments, the grain size of the of the tungsten carbide component may be on the order or microns or sub-micron in size, for example about 0.5 micrometers to about 2 micrometers, and including about 1.0 micrometers to about 1.4 micrometers, and further including about 1.2 micrometers. The slotted member 300 further includes a selected number of slots or slits that are formed through the slotted member 300, such as a first slot 340, a second or middle slot 344, and a third slot 348. The slots 340, 344, 348 may be used to form selected x-ray beams, volumes, or areas, such as fans, when positioned over the aperture 232 of the stage 228. As discussed above, and further herein, the slotted filter 260 may be used to generate or form a beam of x-rays relative to the subject 28 for collecting image data thereof.

Generally, the slotted filter 260 may be positioned such that the first sheet 304 is positioned away from the subject 28 and generally near the source of the x-rays (e.g. the x-ray tube 190). Accordingly, the x-rays may generally pass through the slotted filter member assembly 260 generally in the direction of the vector or arrow 94 first engaging the first layer member 304 and finally engaging or passing through the second layer sheet 308. Generally, the slotted member 300 will block all or substantially all of the x-rays that pass through the first sheet 304 save for the x-rays that pass through the slots 340, 344, 348. Accordingly, x-rays that engage the detector 78 when passing through the slotted filter member 260 are limited to only those x-rays that pass through the slots 340, 344, 348. It is understood, however, at noted above the members 304, 308 may be placed in any appropriate manner relative to the slotted member 300. Further, the materials selected for the first and second members 304, 308 may assist in refining and/or selecting spectral content of the x-rays that pass through the filter assembly 260.

The slot filter assembly 260 includes the slotted member 300, as discussed above. As illustrated in FIGS. 4B and 4C the slotted member 300 includes various features including the slots 340, 344, 348. The slotted filter 300 includes a main body or member 352 through which the slots 340, 344, 348 are formed. The main body 352 may have a selected thickness 354, the thickness 354 may be about 0.01 in to about 1 in, including about 0.01 in to about 0.1 in, and further including about 0.07 in to about 0.1 in and further about 0.09 in (about 2.2 mm). It is understood that the thickness 354 of the main body 352, either alone or in combination with the other filtered layers 304, 308, may be used to form or define the x-rays that pass through the filter assembly 260. The main body 352 may include further dimensions for various purposes, however, these dimensions may be based upon the size of the aperture 232, the size of the filter assembly 224, or other appropriate constrictions. Nevertheless, in various embodiments, the main plate 352 may include a length dimension 356 between terminal ends of about 0.5 in to about 2 in, and including about 1.4 in (35 mm). A width dimension 360 may be about 0.1 in to about 2 in, and further including about 0.9 in (22 mm). The main plate 352 of the slot filter member 300 may include various configurations, such as chamfered or angled corners 364 that may form an angle of about 45 degrees relative to the ends of the main body 352. Again, it is understood, that the filter assembly 260 may include various configuration for fitting in a selected imaging system, such as the imaging system 36, and specific shapes of the exterior may be based upon configurations of the imaging system 36. The thickness 354, however, may be selected to ensure minimal or no x-ray radiation passes through the filter assembly 260 other than through the slots 340, 344, 348.

With continuing reference to FIG. 4A and FIG. 4B, and particular reference to FIG. 4C, the main slot filter body member 352 has a thickness 354. The thickness 354 is defined by or between the two surfaces 320 and 330. In various embodiments, the surface 320 may be a surface that is positioned closest to the source of the x-ray radiation while the second surface 330 is the surface positioned closest to the subject 28. It is understood that the surfaces may also be referred to, respectively, as the top surface 320 and the bottom surface 330. It is understood, however, that top and bottom are merely exemplary and not intended to define an absolute position of the filter body member 352.

The filter body member 352 including the three slots includes the middle slot 344 and two edge slots 340, 348. Each of the slots are formed to between and through the two sides 320, 330, as discussed further herein. Each of the three slots may be formed through the member 352 in an appropriate manner, such as electrical-discharge machining or other appropriate tool (e.g. a router or punch). It is further understood that the slots may be forged or otherwise cut into the member 352. Nevertheless, near or at the first surface 320 each of the three slots 340, 344, 348 are formed by two respective side walls each, for example the first slot 340 is formed between the side walls 370 and 374; the second slot 344 is formed between the side walls 378, 382; and the third slot 348 is formed between the side walls 386 and 390. It is understood, as illustrated in FIG. 4C, that the side walls extend between two ends 357 and 358 of the member 352. The side walls for each of the slots 340, 344, 348 are generally equal distances apart and substantially parallel along the length of the respective slots. Further, the slot walls are generally straight and parallel relative to one another. It is understood, however, that certain tooling cause various portions of the slots to be of a slightly different dimension, such as an entry or exit plunge cut to initiate or end the slot. However, each of the slots 340, 344, 348 are generally formed to have a dimension 398 of about 0.001 in to about 0.1 in, including about 0.009 in to about 0.03 in, and further including about 0.025 in to about 0.01 in, and further including about 0.02 in (about 0.5 mm). The width 398 of the slots 340, 344, 348 may be substantially identical for each of the slots is generally a dimension between the interior surfaces of the respective opposed walls of the respective slots.

The respective walls forming the respective slots at the first surface 320 may each have a center between the respective walls. For example the slot 340 may have a center line or axis 400, the second slot 344 has a center axis 404 and the third slot 348 has a center axis 408. Each of the axes 400, 404, 408 may be of a point that is at a center between the respective walls and substantially perpendicular to the surface 320. The center points or axes 400, 404, 408 are generally or substantially perpendicular the surfaces 320, 330 and may be spaced a selected distance apart such as a distance 412. The distance 412 may be the same between each of the slots and may be about 0.01 in to about 1 in, and further about 0.1 in to about 4 in, and further about 0.318 in to about 0.322 in (8.0 mm to about 8.2 mm) apart. The distance 412 may be selected based upon various parameters, such as the size of the slot member 352, the size of the aperture 232 in the filter stage 228, or other appropriate considerations. Accordingly, the distance 412 may be selected based upon various parameters. It is understood, however, that the spacing 412 between the respective slots 340, 344, 348 may be a substantially precisely selected for various imaging gathering techniques and/or stitching, as discussed further herein.

The respective central axes 400, 404, 408, as discussed above, are defined or may be defined by a point that is at a center between the respective walls at the first side 320 and substantially orthogonal to the first side 320. The central or second slot 344 may have the side walls 378, 382 that are substantially parallel with the central axis 404 and substantially perpendicular to the surface 320. Accordingly, the central axis 404 may extend through the plate member 352 substantially parallel with the side walls 378, 382. The distance or width 398, therefore, may be substantially split in half or divided by the central axis 404.

The edge slots 340 and 348, however, may have respective central axes 420 and 424 that extend substantially parallel to the respective side walls 370, 374 and 386, 390 and not perpendicular to the surface 320. The central axes 420, 424 may form an angle relative to the respective center point axis 400, 408. For example, the first slot 340 having the central axis 420 may form an angle 428 relative to the center point axis 400. The angle 428 may be about 5 degrees to about 10 degrees and further about 6 degrees to about 8 degrees, and further about 7 degrees. The central axis 424 may also form an angle 432 relative to the center point axis 408. The angle 432 may be about 5 degrees to about 10 degrees, and further about 6 degrees to about 8 degrees, and further about 7 degrees. Accordingly, the angles 428, 432 may be substantially similar or identical as an internal angle between the respective central axes 420, 424 and the center point axes 400, 408. The angles 428, 432 may also be formed relative to either of the surfaces 320, 330 as the center point axes are substantially perpendicular to both surfaces 320, 330.

The angles 428, 432 may assist in allowing x-rays to pass from the source 190, as schematically illustrated in FIG. 4C, through the respective slots 340, 344, 348 without any or substantial distortion due to interaction with the respective side walls 370, 374, 379, 382, 386, 390. As illustrated in FIG. 4C and as discussed above, the x-rays may be emitted from the source tube 190 in substantially a cone shape. Accordingly, x-rays that travel substantially normal to the surface 320 will pass through the central slot 344 along the central axis 404 without substantial or any interaction with the side walls 378, 382. Also due to the respective angles 428, 432, the x-rays that are near an edge of the cone 90 may pass through the edge slots 340, 348 without substantial interaction with the respective side walls 370, 374, 386, 390 due to the respective angles 428, 432.

The slot filter member 300 of the slot filter assembly 260, according to various embodiments, may allow for a formation of three x-ray fans or areas of x-rays including a first fan 440, a second fan 444, and a third fan 448 due to the respective slots 340, 344, 348. The three fans are formed by the slot filter 260, including the main member 300, filter x-rays from the source 190 save for the area of the slots 340, 344, 348. In other words, the slot filter 260 filters the x-rays from the source 190 and allows the x-rays to pass through the slots 340, 344, 348 to form the fans 440, 444, 448. In various embodiments, the slot filter assembly 260, such as the main body 300, is a distance 450 from the source 190. The distance 450 may be about 50 mm to about 100 mm, including about 60 mm to about 80 mm, further including about 68 mm to about 72 mm.

As discussed further herein, the three fans 440, 444, 448 allow for generation of selected image projections due to an imaging area on the detector 78. Further, due to the angles 428, 432, as discussed above, the first and third fans 440, 448 are not substantially distorted due to interaction of x-rays with the plate member 352. It is further understood that the numbering of the slots 340, 344, 348 and the respective fans 440, 444, 448 is merely for clarity of the current discussion, and not intended to require any particular order. Further, it is understood, that the filter member 352 may include a selected number of slots, such as less than three or more than three and three is illustrated and discussed for the current disclosure. It is understood, however, that the three slots 340, 344, 348 allow for the generation of a long view in an efficient and fast manner, as discussed further herein. Including a selected different number of slots may allow for a generation of a different number of intermediate images as discussed herein, but is not required.

As discussed above, the slot filter assembly 260 may be used in the imaging system 36 to acquire images of the subject 28. Returning reference to FIG. 2, the SDU 98 may be moved around the subject 28 within the gantry 70. It is understood that the SDU 98 may be moved in any appropriate manner, and that the imaging system 36 is exemplary. Nevertheless, in various embodiments, the SDU may be rotated from a first position to a second position, such as about 90 degrees apart. For example, as illustrated in FIG. 2, a first position of the SDU 98 may include the source 74 directing the x-rays along the cone 90 for the detector 78 which may be generally an anterior to posterior (AN) orientation relative to the subject 28. The SDU 90 may be rotated 90 degrees, such that the source is at a second source position 74' and the detector may be moved to a different position such as at a second detector position 78'. The SDU 98 may be positioned at either or both of the positions and a line scan of the subject 78 may be formed.

The line scan may include moving the gantry 70, including the SDU 98, along the long axis 106 of the subject 28 which may also be referred to as a Z axis or Z direction of the imaging system 36 generally in the direction of the double headed arrow 114, as illustrated in FIG. 1. The detector 78 may, therefore, be moved in a linear direction substantially with movement only in the direction of the double headed arrow 114 along a Z axis. The acquired image data may be used to form a long film or long view of the subject 28 with the image data acquired at one or both of the positions of the detector 78, 78' as illustrated in FIG. 2. The use of a slot filter 260 may be used to generate a plurality of views along the Z axis, as discussed further herein.

Figure 5B:
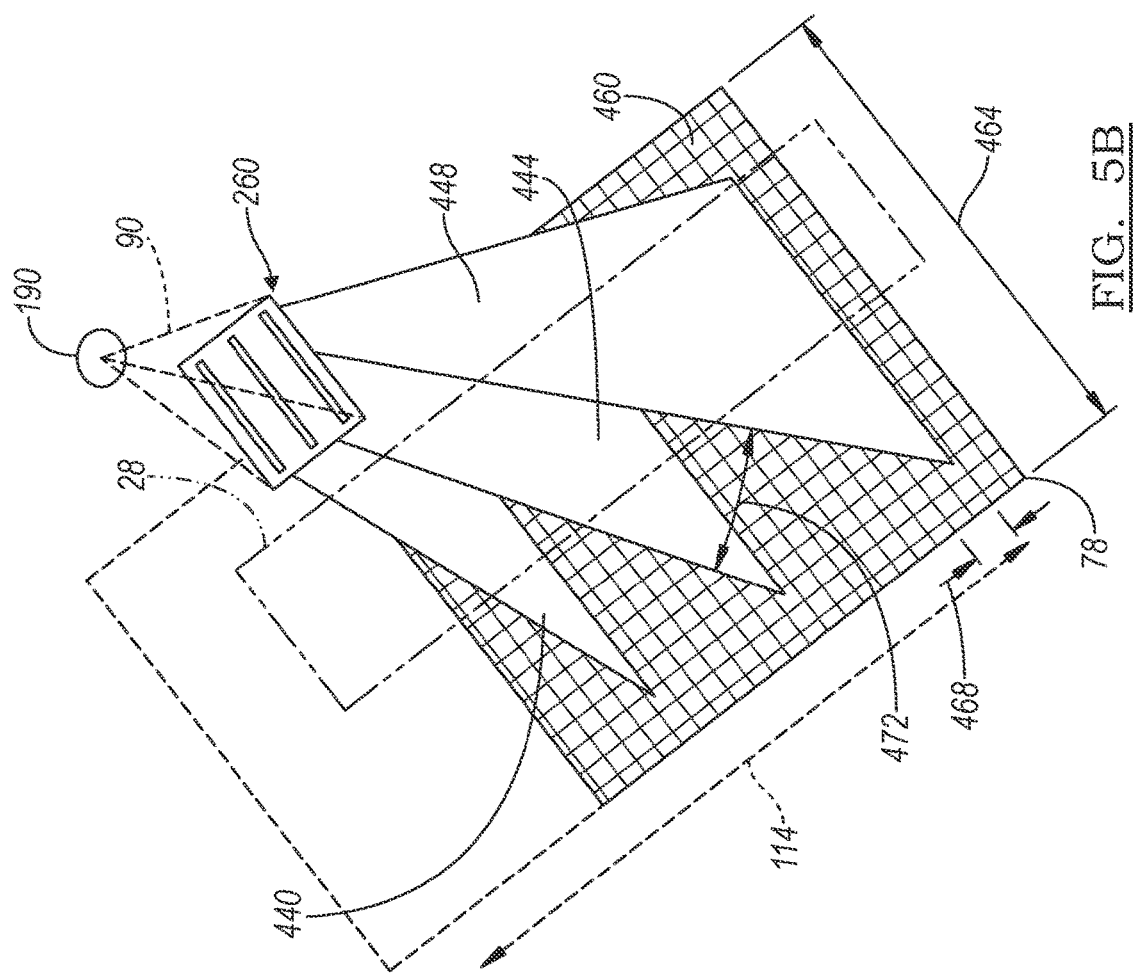
FIG. 5A and FIG. 5B are schematic illustrations of a slot filter assembly relative to a source and detector.
Figure 5A:
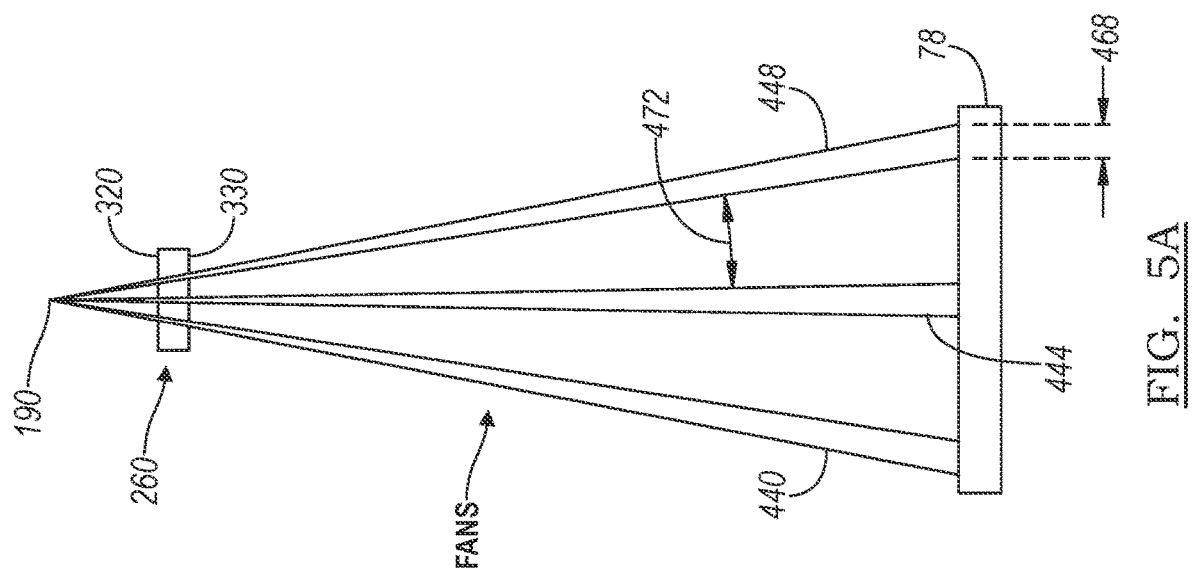

As illustrated in FIG. 4C and with further reference to FIG. 5A and FIG. 5B, the slot filter assembly 260 may be used to form the three fans 440, 444, 448 that reach or have attenuations that are detected by the detector 78. Each of the fans 440, 444, 448 directly or have attenuations that impinge or contact the detector 78 at a substantially narrow position or area. As illustrated in FIG. 5B, the detector 78 may include a plurality of excitable or detector regions or portions 460. The detector regions 460 may also be referred to as pixels and may relate to a single picture element (pixel) that is illustrated on the display 44 in the image 40.

The entire cone 90 from the source 74 may have an area that would excite or impinge upon the entire surface of the detector 78. However, the individual fans 440, 444, 448 generally impinge upon only a narrow band of the pixels 460. It is understood that the number of pixels excited may include an entire width 464 of the detector 78, but limited to only a selected length 468 of the detector. For example, the respective fans 440, 444, 448 may impinge upon, assuming that no object or subject is within the path of the x-rays (e.g. an air scan), about 10 about 100 pixels. The number of pixels excited in the dimension 468 on the detector 78, however, may be augmented or adjusted depending upon the distance from the detector 78 of the filter assembly 260, the width of the slots (340, 344, 348), or other appropriate considerations. Nevertheless, as illustrated in FIG. 5A and FIG. 5B, each of the respective fans 440, 444, 448 will impinge upon the detector 78 at a substantially narrow position and excite a length 468 of pixels that may be along a substantially entire width 464 of the detector 78. The width of the slots 398 that causes the length of pixels 468 to be excited (e.g. generate image data) limits or eliminates parallax distortion within the image portion collected with the imaging system using the slot filter 300, as discussed herein.

Further, as illustrated in FIG. 5A and FIG. 5B, the detector 78 may be impinged upon by the three fans 440, 444, 448 substantially simultaneously from a single position of the source tube 190 along the Z axis generally in the direction of the double headed arrow 114. The detector 78, therefore, may output three different images or image data for three different positions of the x-ray at each single position of the source tube 190. Movement, of the source tube 190 of the source 74 generally in the direction of the double headed arrow 114, however, may create a plurality of three views along the Z axis, as discussed further herein. Each of the fans 440, 444, 448 may be separated by a selected distance, which may also be an angular distance 472.

The imaging system 36 may be used to generate images of the subject 28, for various purposes. As discussed above, the images may be generated of the subject 28 for performing a procedure on the subject 28, such as a spinal fusion and/or implants relative to or adjunct to a spinal fusion. In various embodiments, therefore, user 24 may evaluate the subject 28 by viewing and evaluating images of the subject 28 for determination of placement of selected implants, such as pedicle screws. Accordingly, the imaging system 36 may be used to acquire an image of the subject 28.

The image system 36 may be used to acquire one or a plurality of projections. As further discussed above, the detector 78 detects x-rays that pass through or are attenuated by the subject 28. Generally, however, the detector 78 detects a single projection at a time. The imaging system 36, including the control system 64, either alone or in combination with the processor system 48 may generate a long film or long view of the subject 28 by accumulating (e.g.

stitching) a plurality of projections of the subject 28. In various embodiments, the imaging system 36, therefore, may be operated to acquire a plurality of images.

Turning reference to FIG. 6, a method 500 of acquiring images, such as a long view of the subject 28, is illustrated. The method 500 may include or start in start block 510. The method 500 may then include positioning of the subject 28 in block 514. Positioning the subject 28 in block 514 may include positioning the subject 28, which may be a human patient, on the support 32 relative to the imaging system 36. Also, as discussed above, the imaging system 36 may be a mobile imaging system, thus positioning the subject 28 in block 514 may include moving the imaging system 36 relative to the subject 28. In particular, positioning the subject 28 may include positioning the subject 28 relative to a center or isocenter of the imaging system 36 such as within the gantry 70 and between the source 74 and the detector 78.

After positioning the subject 28 in block 514, acquisition parameters may be set or input in block 518. Inputting acquisition parameters may include the selected length of the view of the subject 28, the resolution required or selected, specific movement parameters of the imaging system 36, or other appropriate input parameters. For example, the user 24 may input a length or number of vertebrae to be imaged. The controller 64 may then determine an amount of movement, such as a length in the axial direction along the long axis 106 of the patient and the direction of the double headed arrow 114. Further, the user 24 may select to acquire image data that may be reconstructed into a three-dimensional model, as discussed herein. Accordingly the user 24, either manually or automatically with the control system 64, or other appropriate control or processor system, may determine acquiring images of the subject 28 along at least the AP view and a lateral view to allow for reconstruction of a three-dimensional model. It may further be understood that only a selected two-dimensional view may be acquired or selected of the subject 28 and therefore only a single line scan may be acquired. It is further understood that the imaging system 36 may be used to acquire any appropriate type of image of the subject 28 and that a line scan for long view is merely exemplary. Nevertheless, a line scan may be acquired of the subject 28 by moving the SDU 98 in a generally linear manner or direction from a start point to an end point. In various embodiments, an AP view may be collected in a first direction along the arrow 114 and the SDU 98 may be rotated 90 degrees to collect a lateral view on a return path for the same length along the arrow 114.

After setting acquisition parameters in block 518, the projections of the subject are acquired in block 522. The acquisition of the projections may include acquiring a slot or fan projection in a line scan of the subject 28. The acquisition of the projections may include acquiring the three fan projections at a plurality of locations of the source and detector and the SDU 98 along the line path, such as along the longitudinal axis 106 of the subject 28. The number of acquisitions may be selected based upon the quality desired or selected for the final long view, including insuring an appropriate focus, minimizing or eliminating distortions (e.g. edge distortions), or other appropriate considerations.

After the acquisition of the projections in block 522, a reconstruction of a long view also referred to as a long film, is made in block 526. The reconstruction of the long view may include various sub-steps and sub-algorithms, as discussed further herein, to form a selected reconstruction, such as long view of the subject 28. The reconstruction may include various features such as ensuring an appropriate focus, iterating the plurality of projections, or the like. The plurality of projections may then be stitched together into a long view, either sequentially or to provide a plurality of long views, as discussed herein.

The long view may then be optionally saved in block 530. Saving the long view in block 530 may be saving the long view in any appropriate memory, such as the imaging system memory 68 and/or the processing system memory 58. It is understood that saving the long view is optional and is not required. The long view may then be displayed on a selected display device in block 534, such as on the display device 44. The image 40 may include the long view reconstructed in block 536 or include only the long view reconstructed in block 526. The displaying of the image in block 534, however, may also be used to illustrate the position of the instrument 144, such as with the instrument icon or representation 180 that is discussed above.

The procedure 500 may then end in end block 540. Ending in block 540 may include stopping operation of the imaging system 36 and allowing a procedure to continue, as discussed above. In various embodiments, the acquisition of the long view may be used for planning a procedure on the subject 28, such as prior to a procedure or in an operating room made during an intermediate step of the procedure. Further the long view may be acquired for various purposes, such as conformation of a step of the procedure (e.g. placement of a first pedicle screw or other appropriate number of pedicle screws), or other steps. Accordingly, ending in block 540 may be ending the acquisition of projections and reconstruction of a long view for display and use by the user 24, or other appropriate user.

With continuing reference to FIGS. 1-6, and additional reference to FIG. 7 the reconstruction of the long view in block 526, illustrated in FIG. 6, may include various sub-steps and/or sub-portions as illustrated in FIG. 7. Accordingly, FIG. 7 illustrate details of the reconstruction of the long view in block 526 and may be incorporated into the method 500, discussed above. The method 500, therefore, may include the sub-portions as illustrated in FIG. 7.

With continuing reference to FIG. 7, the reconstruction of the long view (also referred to herein as reconstructed long view) generally includes the portions or sub-portions, as illustrated in block 526. It is understood that various features and steps may be included as instructions, such as with an algorithm, that are executed by one or more processor or processor systems. For example, the imaging system processor 66 and/or the processing system 48 having a processor 56, may execute instructions to generate the long view based upon the plurality of acquired projections from block 522. As discussed above, operation of the imaging system 36 may acquire the plurality of projections in block 522, such as with the slot filter assembly 260. Accordingly, the imaging system 36 may generate projections that are based upon x-rays detected by the detector 78. Inputting the acquired projections in block 550 may initiate the reconstruction process 526, as discussed above and herein, the input of projections from three slots is exemplary and more or less is possible.

The x-ray projections may be acquired at the detector 78 with each of the three slots that generate the respective fans 440, 444, 448. With continuing reference to FIG. 7, and additional reference to FIG. 8 each of the three fans 440, 444, and 448 will generate three separate series of images or projections 560, 564, 568, respectively. Each of the series of projections includes a plurality of projections that are acquired substantially simultaneously. For example, the first series 560 may include a first image slice 560$i$ that will be acquired at the same position of the SDU 98 as a first image 564*i* and 568*i* of each of the respective fans 440, 444, 448. As the SDU 98 moves in the selected direction, such as along the axis 106 in the direction of the arrow 114, a plurality of projections are acquired through each of the slots due to each of the fans 440, 444, 448. Accordingly, three series 560, 564, 568 of projections are acquired due to movement of the imaging system 36 along a selected line scan. These series of projections 560, 564, 568 are the input projections in block 550 from each of the three slots. As discussed further herein, although each of the slots and the respective fans 440, 444, 448 are used to generate respective series of projections 560, 564, 568, all of the image projections may be used to generate the long view that is reconstructed in block 526. Accordingly, the input of the x-ray projections from all three slots in 550 may include input of all three series of projections 560, 564, 568 which may be analyzed or evaluated separately, in various portions of the reconstruction of 526, and then combined to form the final long view, as discussed further herein. Each of the image slices for each of the series (e.g. 560*i*, 564*i*, and 569*i*) generally and/or substantially are free of parallax distortion due at least in part to the width of the slot 398 and the corresponding length 468 excited on the detector. Thus, the slices may be clearer and have less error or distortion due to the slice width 398.

The procedure 526, further includes an input of a motion profile of the imaging system 36 in block 578. The input of the motion profile of the imaging system in block 578 may include the distance traveled, time of distance traveled, distance between acquisition of projections, and other motion information regarding the imaging system 36. The motion profile information may be used to determine and evaluate the relative positions of the projections for reconstruction, as discussed herein.

Figure 8:
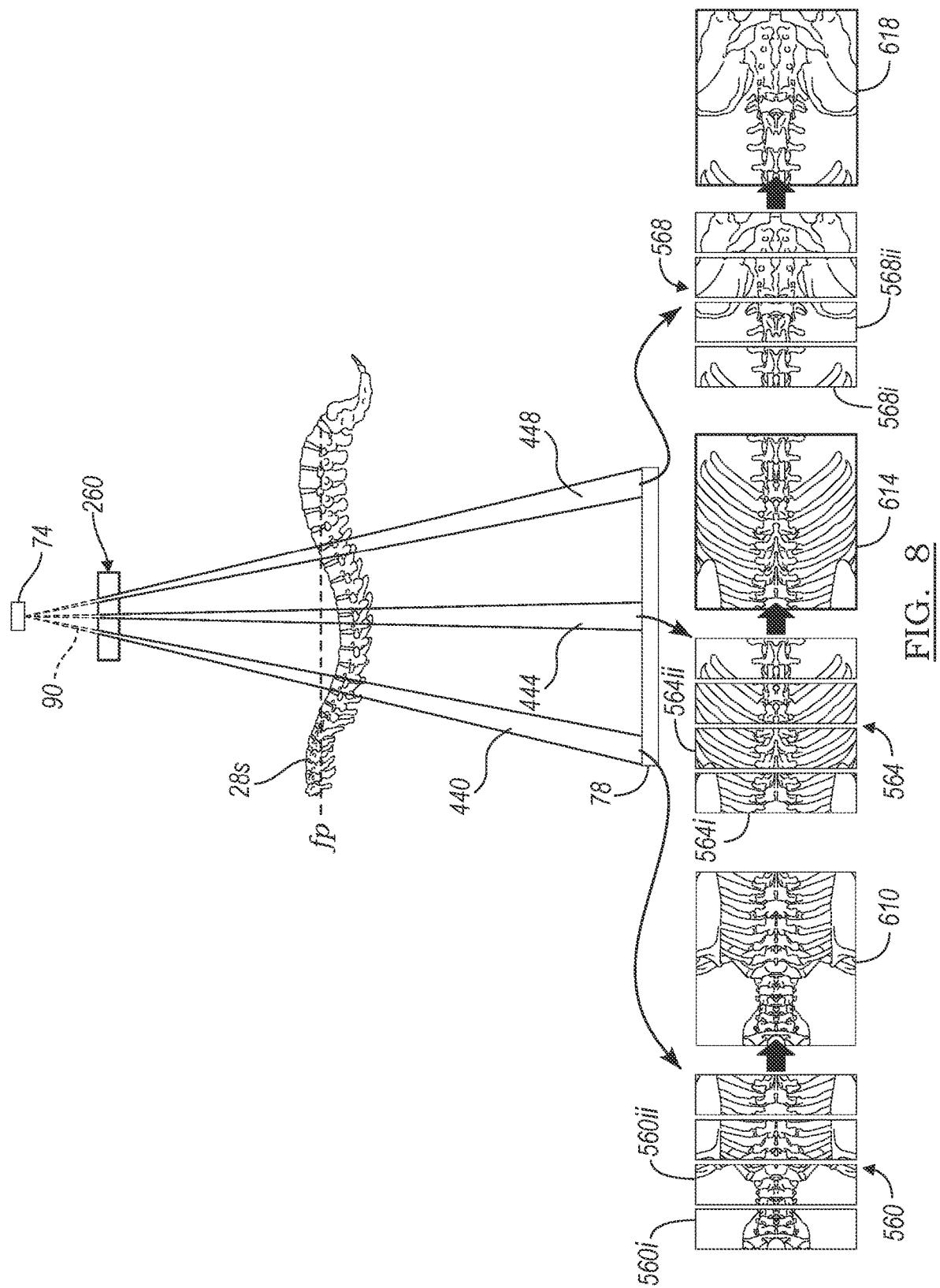
FIG. 8 is a schematic illustration of acquiring a plurality of projections in intermediate images, according to various embodiments.

After the input of the x-ray projections from block 550, a plane of focus may be set, such as arbitrarily, at a selected axis or line such as focus plane (fp)=0 in block 590. A fp=0 may be defined as the isocenter of the imaging system 36. With continuing reference to FIG. 7 and FIG. 8, the fp may be defined relative to a portion being imaged, such as a spine 28*s* of the subject 28. The FP=0 may be an arbitrary position and used to stitch together or put together the series of projections into selected intermediate images for each slot in block 600.

The generation of the intermediate images at the selected FP may generate the intermediate images for each of the series 560, 564, 568, as illustrated in FIG. 8. Accordingly, a first intermediate image 610 may be generated based upon the first series of projections 560. A second intermediate image 614 may be based upon the series of projections 564 and a third intermediate image 618 may be based upon the third series of projections 568. Each of the intermediate images 610, 614, 618 may be stitched together using generally known techniques such as image blending, registration, and view manipulations. These may include blending various portions of images that are near matches (e.g. determined to be similar portions) to achieve continuity. Registration includes matching or identifying identical portions of two or more images. Manipulations allow for altering different images or portions thereof, as discussed herein.

The plurality of projections, also referred to as image data portions, in each of the series, such as the first series 560, are taken at a selected rate as the SDU 98 moves relative to the subject 28. As illustrated in FIG. 8, the subject 28 may include the spine 28*s*. As the SDU 98 moves, for example, the fan 440 is moved a selected distance, such as 1 centimeters (cm) per projection acquisition. Accordingly, each of the image projections, such as the image projection 560*i*, may be the width on the detector of the fan 440 and a second image projection 560*ii* may be 1 cm from the first image projection 560*i* and also the width of the fan 440 on the detector 78. A selected amount of overlap may occur between the two image projections 560*i* and 560*ii* that allows for stitching together into the intermediate projection or image 610, as is generally known in the art. Each of the series of projections 560, 564, 568 (which may each include image data portions), therefore, may be stitched together at the respective focus plane to generate the intermediate images 610, 614, 618. As discussed above, the focus plane may be initially set at 0 or arbitrarily set at 0 which is generally the isocenter of the imaging system 36 that acquired the plurality of projections 560, 564, 568.

After the intermediate images are generated at the FP=0 for each slot in block 600, a registration of the intermediate images for each slot and determine a translation d occurs in block 680. With continuing reference to FIG. 7 and additional reference to FIG. 9A and FIG. 9B, the intermediate images are generated based upon the plurality of projections due to movement of the SDU 98. As illustrated in FIG. 9A, a schematic representation of a first movement or distance d1 is illustrated. d1 may be the d, discussed above. d1 is the distance that the source 74 may move from a first position 74*i* to a second position 74*ii*. The slot filter 260 may also, therefore, move from a first position 260*i* to a second position 260*ii*. As illustrated in FIG. 9A, the second fan 444 at the first position of the slot filter 260*i* and the first fan 440 at the second position of the slot filter 260*ii* may intersect or cross at a focus plane FP=1.

Figure 9B:
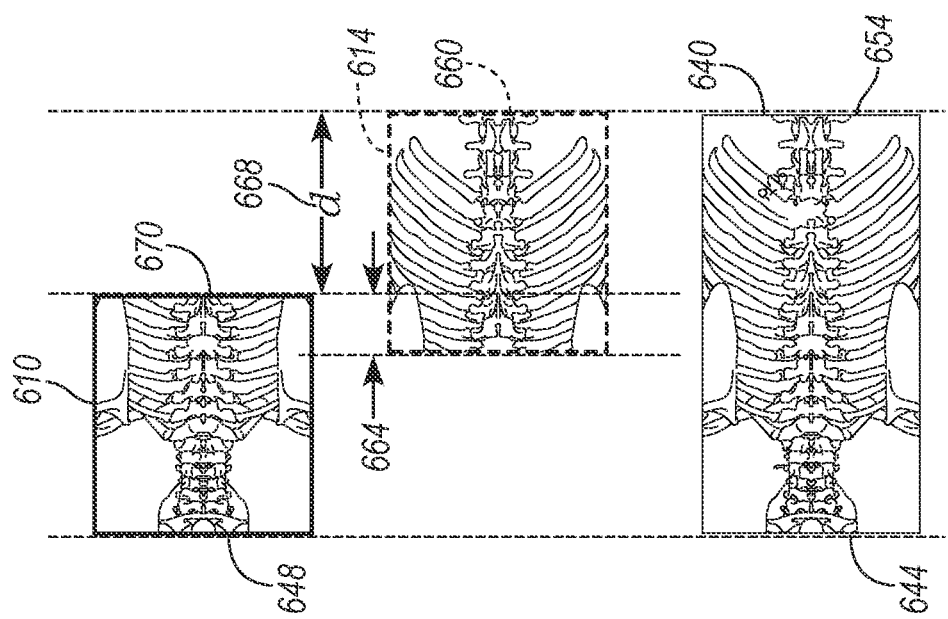
FIG. 9B is a schematic illustration of a registration of intermediate images.
Figure 9A:
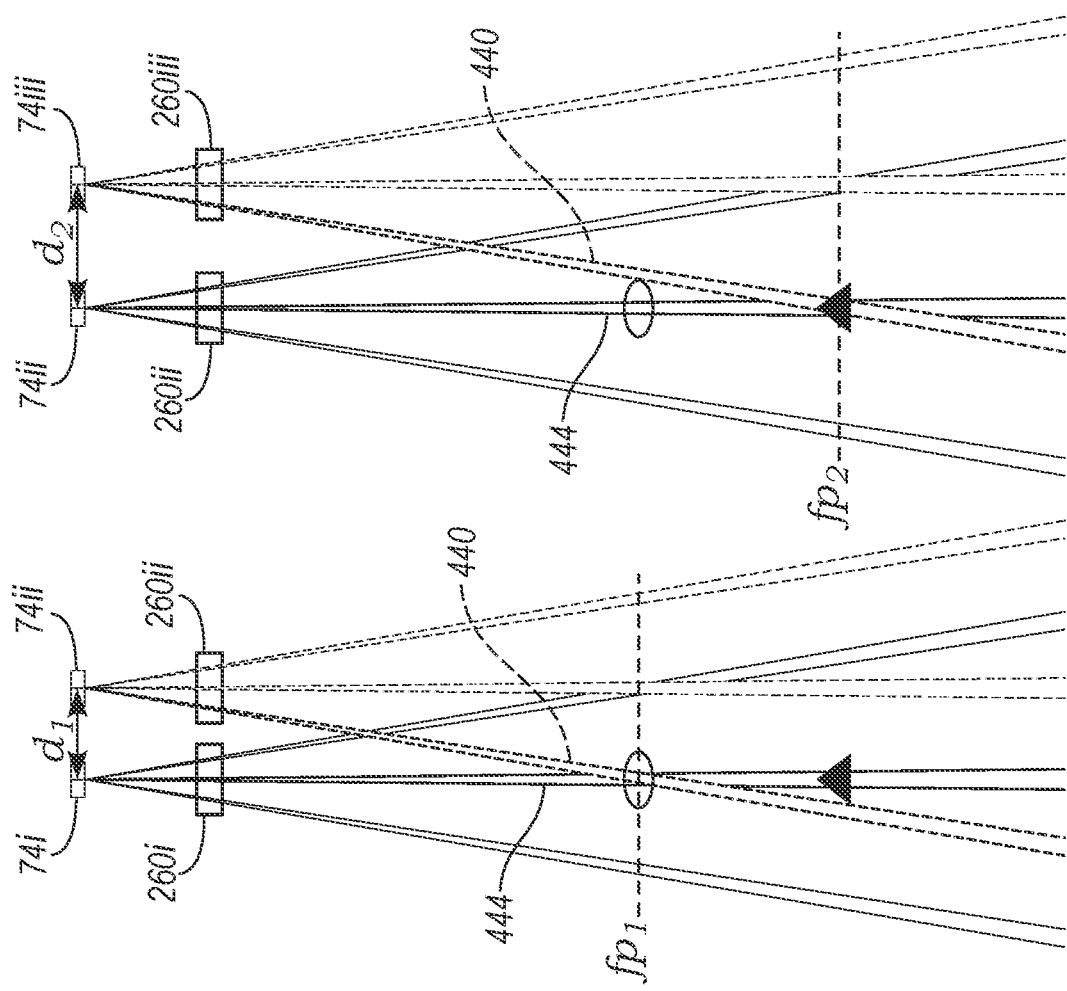
FIG. 9A is a schematic illustration of a focus plane relative to a slot filter assembly.

As illustrated in FIG. 9B, the source 74 may move from the second position 74*ii* to a third position 74*iii* and respectively the slot filter may move from the second position 260*ii* to a third position 260*iii*. In this movement, a distance d2 may occur. The movement illustrated in FIG. 9B may include the middle or second fan 444 and the first fan 440 intersect at a second focus plane FP=2. It is also understood that each of the other respective fans may also intersect at different positions, and the illustration of the two fans are merely exemplary and discussion of the other fans will not be repeated, but is understood by one skilled in the art.

The position of an intersection of the fans (i.e. a distance from the source tube 190) at the point being imaged may depend upon the position of the object being imaged, such as the spine 28*s*, from the source tube 190. It is understood by one skilled in the art, the spine 28*s* may not be a straight line or extend along a straight line that is substantially parallel to the long axis 106 of the subject 28, even if an isocenter of the imaging system 36 moves along the axis 106. Accordingly, the focus plane FP may move between different positions of the source 74 and the slot filter 260, as illustrated in FIG. 9A and FIG. 9B. Thus, the first distance d1 which may be different from the distance d2 and may also alter the focus plane of the image or projections acquired with the imaging system 36. Nevertheless, the first intermediate image generated in block 600 may assume that the focus plane is at the isocenter of the imaging system 36.

With continuing reference to FIG. 9A and additional reference to FIG. 9B, the first intermediate image 610 and the second intermediate image 614 are displayed. The intermediate images may include all of the intermediate images, including the intermediate images 610, 614, 618 and the discussion of only the first intermediate image 610 and the second intermediate image 614 is merely for clarity of the current discussion. Nevertheless, the intermediate images 610 and 614 may be registered to one another to determine or generate a registered image 640.

The registered image 640 may include a first end 644 that is equal to a first end 648 of the first intermediate image 610 and a second end 654 that is equivalent to a second end 660 of the second intermediate image 614. Accordingly, the registered image 640 may be a composite or overlay of the first intermediate image 610 and the second intermediate image 614. In particular, an area of overlap 664 may be determined or identified between the first intermediate image 610 and the second intermediate image 614. The overlap 664 may be identified such as through feature based registration, mutual information based registration, or other appropriate registration or image matching methods.

As illustrated in FIG. 9B, the second intermediate image 614 has the second end 660 that is a distance 668 from a second end 670 of the first intermediate image 610. The distance 668 may be used or be identified as the distance d of movement of the imaging system and may be used to alter or determine a plane of focus for each of the intermediate images, or a mutual plane of focus for the intermediate images. Accordingly, due to the registration image 640 that is determined by registering the first intermediate image 610 and the second intermediate image 614 the distance d may be determined in block 680.

After determining the distance d, which may be a translation distance and is related to the slot filter spacing (e.g. distance 412), focus plane and region of interest in the subject to be imaged (e.g. anatomical region of interest such as a specific vertebrae or spinous process of a vertebrae), in block 680, an updated plane of focus FP including the distance d may be made in block 684. The distance d, as illustrated in FIG. 9B, may relate to a distance of an adjustment of distance to achieve an alignment of registered elements (e.g. a spinous process) between two or more intermediate images, such as image 610 and 614 to generate the registered image 640. Also, the distance between slots, such as the distance 412, may be used to determine the translation distance d to achieve the registered image 640. The image portions acquired through different slots, even at the same location of the slot filter 260, are at different positions along the subject.

The updated FP, based on the analysis discussed above, including the position of the portion of interest within the subject (e.g. anatomy of interest), may then be input or iterated to generate updated intermediate images with the updated FP in block 690. The updated FP for the iteration to generate the updated image may account for a position of the subject or region of interest from the source 74 between two different intermediate images (e.g. image portions). The generation of the updated intermediate images may be substantially similar to the generation of the intermediate images in block 600, except that the focus plane has been updated based upon the determined translation d. Thus the focus of the intermediate images may be increased or refined due to a determination of the focus plane in light of the translation of the images, as determined above as illustrated in FIG. 9B. The generated updated images in block 690 may then be combined in the combining of intermediate images with a weighting function in block 700. As discussed above and herein, including three intermediate images based on three slots is merely exemplary, and more or less may be allowed or used.

Prior to the generation of the combining in block 700, however, a determination of whether further updated intermediate images may be made in block 692. For example, at least two iterations may occur to determine if a selected minimum is reached. If a minimum is not reached, a further iteration may occur. Regardless of the determination, a decision of whether a further update of the fp may be made in block 692. If an update is made, a YES path 694 may be followed and the fp place may be updated in block 684 and the process may iterate. If no further update is needed or selected, a NO path 696 may be followed to combine the three intermediate images in block 700.

Figure 10:
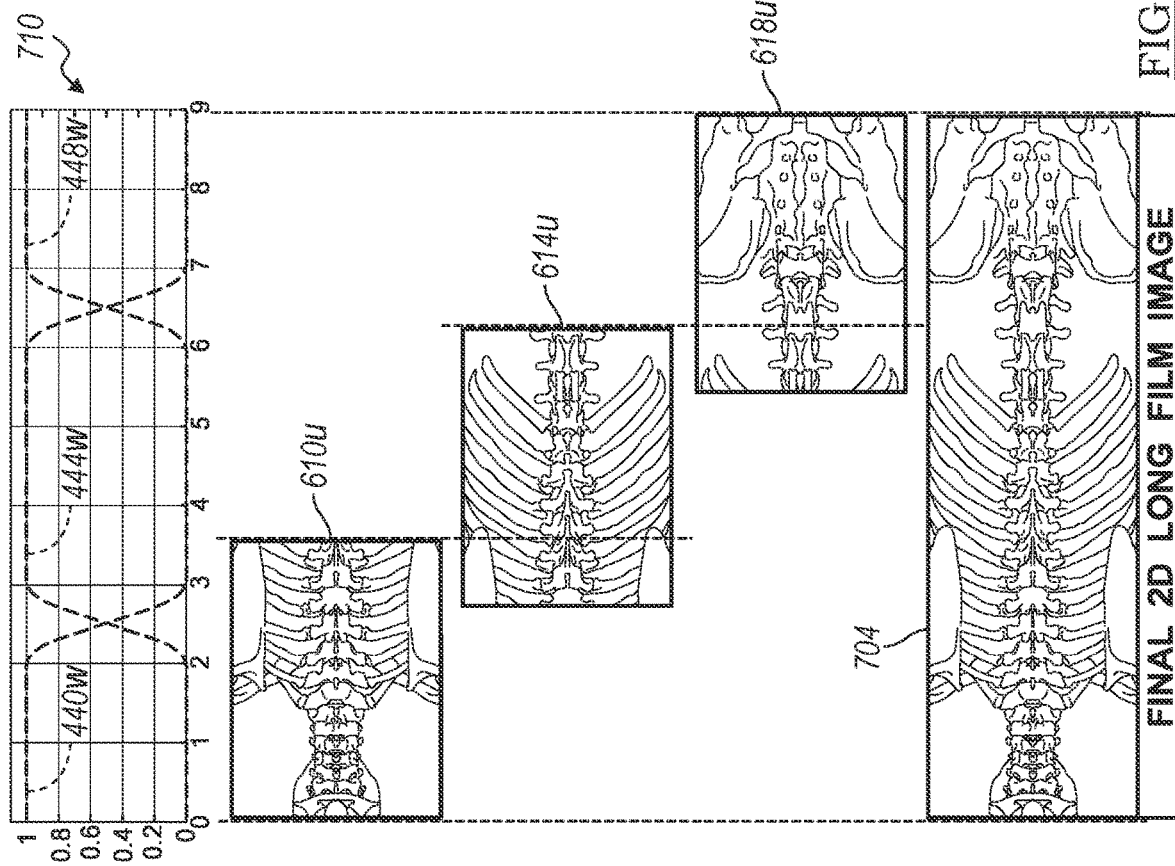
FIG. 10 is a schematic illustration of a formation of a long view with a weighting function.

With continuing reference to FIG. 7 and additional reference to FIG. 10, the intermediate images that are updated in block 690 may include the first updated intermediate image 610u, a second updated intermediate image 614u, and a third updated intermediate image 618u. As discussed above, each of the three intermediate images 610u, 614u, and 618u may then be combined to generate a first or initial long view or long film image 704.

The generation or merging of the various intermediate images, such as each of the three intermediate images 610u, 614u, and 618u, may include various steps and features. In various embodiments, an initial deformation of various features may be made when generating each of the three intermediate images 610u, 614u, and 618u. As noted above, each of the three intermediate images 610u, 614u, and 618u may be generated based on a plurality of projections. Thus, each of the three intermediate images 610u, 614u, and 618u may include a similar or same feature (e.g. vertebrae). The amount of deformation to generate each of the three intermediate images 610u, 614u, and 618u may be determined and used in further merging procedures.

According to various embodiments, a weighting function 710 may be used to assist in the combining of the updated intermediate images 610u, 614u, and 618u to generate the initial long view image 704. The weighting function 710 is graphically illustrated in FIG. 10. A first weighting function for the first fan 440w illustrates that pixels or image portions may be weighted more for the left most portion of the long view due to the position of the fan 440. The intermediate or central fan 444 may have the function 444w that will weight the pixels for the middle of the long view 704 more from the updated image 614u due to the position of the fan 444. Finally, the fan 448 may have the function 448w to weight the pixels furthest to the right or at the end due to the position of the fan 448 in the long view 704. It is understood that other appropriate stitching functions may be used to generate the initial long view 704 and that the weighting function 710 is merely exemplary. Further, a greater weight may be given to the selected intermediate image 610u, 614u, and 618u that has the least deformation when generating the long view. Further, selected deformations, such as geometric deformations, may be made when generating the long view.

In various embodiments, the initial long view 704 may be output as the long view or a long view in block 720. The long view output in block 720 may be saved, such as saving the long view in block 530 and/or displayed in block 532, as discussed above in the process 500 illustrated in FIG. 6. In various embodiments, however, various normalizations and/or processing may be applied to the initial long view 704 prior to the output of the long view in block 720 such as for image enhancement and/or clarity.

With continuing reference to FIG. 7, various procedures may be performed prior to the output of the final 2D long film or long view image in block 720. After the combination of the three intermediate images with the weighting functions, various processing steps may be performed prior to displaying and/or saving the long view image. For example, applying an air normalization in block 730 and/or further post processing for visualization in block 740.

Figure 11:
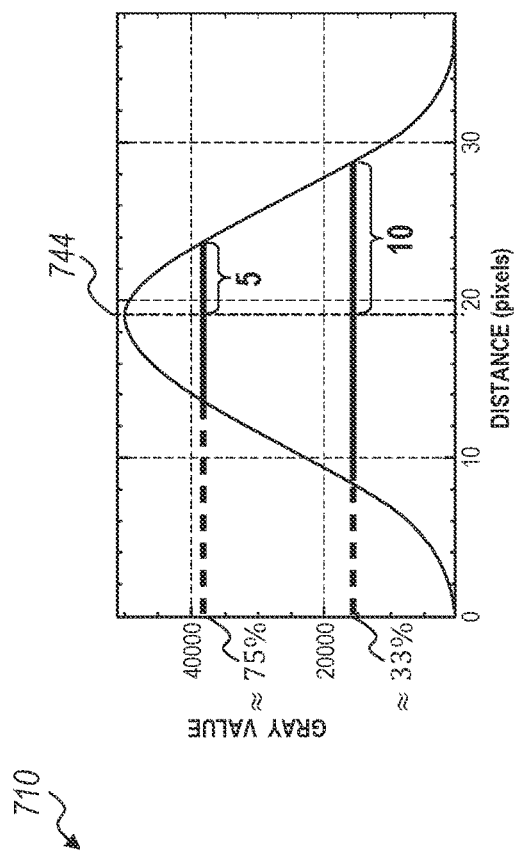
FIG. 11 is a gaussian graph of an intensity plot relative to a detector with a fan x-ray.

The air normalization may account for or minimize effects of the slot filter assembly 260. As illustrated in FIG. 5A and FIG. 5B the fan, for example the fan 448, contacts or impinges upon the detector 78 in the length distance 468. The distance 468 is a small portion of the detector 78. Further, due to the narrow dimension of the fan 448 and, therefore, the small number of pixels contacted on the detector 78, an image or pixel intensity may drop off quickly, such as in a gaussian fashion as illustrated in FIG. 11, from a peak intensity pixel or point 744.

The peak intensity 744 may be at a center of the fan 448, such as the center of the distance 468 at a pixel or point on the detector 78. Within five pixels from the center pixel (i.e. a width of 10 pixels, including the peak intensity pixel) an intensity drop off of about 25% (e.g. the $6^{th}$ pixel away may have an intensity of about 75% of the peak intensity pixel 744) may be observed in the pixels outside of the 10 pixels centered on the pixel with the peak intensity 744. Within 10 pixels from the center pixel (i.e. a width of 20 pixels, including the peak intensity pixel) an intensity drop off of about 66% is observed (e.g. the 11th pixel away may have an intensity of about 33% of the peak intensity pixel 744). Accordingly, a narrow band of pixels may include all or substantially all of the intensity due to the fan 448. It is understood, that each of the other fans 440, 444 may include or have the similar pixel intensity drop off.

A mask may be applied to assist in reduce the effect of the intensity drop-off. A mask that is 40 pixels wide may be applied to each image acquired with each of the slots to account for and eliminate those pixels that has substantially no intensity due to the narrow fan widths 440, 444, 448. The images that are acquired are thereby normalized in a reconstruction, such as due to the combination of the intermediate images in block 700, to reduce or eliminate the distortion that may otherwise be observed. For example, upon stitching a plurality of narrow images, such as the image 460i with the image 460ii if the normalization does not occur, the edges of the image may be substantially light or have nearly no pixel intensity relative to center pixels. Without the mask and normalization. when stitched or combined, the combined image may have a "ripple effect" that may be viewed in a stitched image. The ripple effect may alternate between dark and light bands due to the changing pixel intensity over a plurality of stitched images where the amount of pixel intensity drop off is substantial over a narrow ban or width of pixels.

Further post processing for visualization may occur in block 740. Various post processing can include any appropriate post processing to assist in visualization of the combined image from block 700. In various embodiments for example, a normalization or histogram averaging (e.g. of pixel intensities) of the image may occur. For example, the final reconstruction may have the stitched pixel values divided by a cumulative pixel value to assist in reducing or minimizing great variations between high contrast and low contrast areas in the combined image from block 700. Thus the image may be prepared for viewing with further post processing in block 740. The post-processing can include, but is not limited to, enhancing of anatomical features, highlighting anatomical features (e.g. masking), sharpening edges, etc.

Accordingly, in light of the above, the imaging system 36 may be used to acquire a plurality of projections of the subject 28. The plurality of the projections of the subject 28 may be acquired in a linear manner, such as in a first line scan in an AP (anterior to posterior) direction and a second line scan in a lateral direction. The plurality of projections may then be stitched or combined into a single long view or long film view of the subject 28. Various intermediate steps, such as those discussed above, may be performed to assist in performing or generating the single long view. For example, a plurality of slots in a filter may be used to generate a plurality of intermediate images that are then finally stitched together to form the single long view. Nevertheless, the imaging system 36 may be used to generate a long view of the subject 28.

Further each of the slots in the slot filter 260 may allow for the acquisition of a different "view" of the subject 28 during scanning of the subject 28. For example, each of the three fans 440, 444, 448 acquire a projection at a single position of the SUD 98. Accordingly, at each view the perspective of the subject 28 may be different. According to various known techniques, therefore, a three-dimensional model of the subject 28 may be reconstructed using the plurality of views of the subject 28 acquired even during the line scans of the subject. A line scan of the subject, as discussed above, may be a substantially linear movement, such as generally parallel with the long axis 106 of the subject 28. Thus the SDU 98 may not rotate around the subject 28 during the acquisition of the linear scan. Nevertheless, the plurality of projections from the various perspectives may be used to reconstruct a three-dimensional model of the subject 28 using the single or two line scans (e.g. AP and lateral line scans). These plurality of projections from various perspectives may also be used to localize items or features in high-contrast objects, such as bony anatomy or implants. The localized position from each of the more than one slot projections may also be used to generated a three-dimensional model of the subject that is imaged. The different position in the plane determined in each of the projections may be used to generate the 3D model, as ius understood in the art.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A method of creating a long view image of a subject comprising:
    positioning an image detector at a first position relative to a subject;
    moving the image detector along a path relative to the subject from the first position to a second position, wherein moving the image detector along the path includes moving at least one of the image detector or a subject support supporting the subject;
    operating a source to emit x-rays to the image detector at a plurality of image projection positions along the path;
    passing the x-rays through a slot filter before the x-rays reach the image detector;
    collecting a plurality of image data portions at the plurality of image projection positions that are a plurality of intermediate positions along the path and may include the first position and the second position;
    determining an overlap region between at least two image data portions of the plurality of image data portions;
    generating an intermediate image for display based on the determined overlap between the at least two image data portions; and
    wherein the intermediate image includes at least a portion of the long view image and is operable to be greater in at least one dimension than either of the at least two image data portions.

2. The method of claim 1, wherein operating the source to emit x-rays includes emitting x-rays from a single source.

3. The method of claim 1, further comprising:
    selecting a portion of the subject; and
    determining a motion profile along the path for the collecting the plurality of image data portions at the plurality of intermediate positions.

4. The method of claim 3, wherein the determined motion profile relative to the subject includes a rotational motion relative to the selected portion of the subject.

5. The method of claim 4, wherein the rotational motion includes moving the image detector on a rotor within a gantry of an imaging system.

6. The method of claim 5, wherein the slot filter divides the x-rays into at least two beams;
    wherein the at least two beams each are operable to generate different projections of the subject.

7. The method of claim 3, wherein the determined motion profile relative to the subject includes a linear motion relative to the selected portion of the subject.

8. The method of claim 7, wherein the motion profile is operable to generate a focus plane of the image data relative to the subject.

9. The method of claim 8, wherein the focus plane is along an axis of the subject.

10. The method of claim 1, wherein the slot filter divides the x-rays into at least two beams;
    wherein each beam of the at least two beams includes a selected spectra.

11. The method of claim 10, wherein the selected spectra are different for each beam.

12. The method of claim 11, wherein the at least two beams includes three beams;
    wherein each beam includes a selected spectra.

13. The method of claim 10, wherein the selected spectra are different for each beam;
    wherein an intermediate image is generated with projections from each of the at least two beams including an identified feature therein.

14. The method of claim 1, wherein the slot filter divides the x-rays into at least two beams;
    wherein each beam engages a selected different portion of the image detector.

15. The method of claim 14, further comprising:
    providing a detector region as a row as the selected portion of the image detector.

16. The method of claim 1, wherein the slot filter divides the x-rays into at least two beams;
    wherein the image detector includes a plurality of image detector configured to detect at least one beam of the at least two beams.

17. A method of creating a long view image of a subject comprising:
    operating an image detector (i) to move along a path relative to a subject from a first position to a second position, wherein moving the image detector along the path includes moving at least one of the image detector or a subject support supporting the subject and (ii) detect x-rays emitted from a source at a plurality of image projection positions along the path;
    collecting a plurality of image data portions at each image projection position of the plurality of image projection positions along the path that may include the first position and the second position, wherein each image projection position is operable to be collected by passing the x-rays through a slot filter before the x-rays reach the image detector, wherein each image projection position of the plurality of image projection positions is achieved over time;
    generating an image for display based on at least a sub-plurality of image data portions of the plurality of image data portions; and
    providing the generated image for display.

18. The method of claim 17, operating a single source as the source to emit x-rays includes emitting x-rays from a single source.

19. The method of claim 18, wherein the image detector is moved to each image projection position after a selected passage of time.

20. The method of claim 19, wherein the generated image is a three-dimensional image of the subject.

21. The method of claim 20, wherein the three-dimensional image of the subject is generated at least due to a movement of the image detector.

* * * * *

UNITED STATES PATENT AND TRADEMARK OFFICE
CERTIFICATE OF CORRECTION

PATENT NO. : 11,364,006 B2
APPLICATION NO. : 17/140930
DATED : June 21, 2022
INVENTOR(S) : Patrick A. Helm et al.

It is certified that error appears in the above-identified patent and that said Letters Patent is hereby corrected as shown below:

In the Specification

Column 4, Line 28, delete "60," and insert --36,-- therefor

Column 5, Line 7, delete "60" and insert --130-- therefor

Column 5, Line 59, delete "94" and insert --90-- therefor

Column 7, Line 24, delete "26." and insert --36.-- therefor

Column 11, Line 51, delete "90" and insert --98-- therefor

Column 11, Line 56, delete "78" and insert --28-- therefor

Signed and Sealed this
Twentieth Day of September, 2022

Katherine Kelly Vidal
*Director of the United States Patent and Trademark Office*